United States Patent
Miller et al.

(10) Patent No.: US 11,634,463 B2
(45) Date of Patent: *Apr. 25, 2023

(54) METHODS AND COMPOSITIONS FOR TREATING HEMOPHILIA

(71) Applicant: Sangamo Therapeutics, Inc., Richmond, CA (US)

(72) Inventors: Jeffrey C. Miller, Richmond, CA (US); David Paschon, Richmond, CA (US); Edward J. Rebar, Richmond, CA (US)

(73) Assignee: Sangamo Therapeutics, Inc., Brisbane, CA (US)

( * ) Notice: Subject to any disclaimer, the term of this patent is extended or adjusted under 35 U.S.C. 154(b) by 760 days.

This patent is subject to a terminal disclaimer.

(21) Appl. No.: 16/523,328

(22) Filed: Jul. 26, 2019

(65) Prior Publication Data

US 2019/0345208 A1    Nov. 14, 2019

Related U.S. Application Data

(63) Continuation of application No. 15/673,163, filed on Aug. 9, 2017, now Pat. No. 10,407,476, which is a continuation of application No. 14/564,722, filed on Dec. 9, 2014, now Pat. No. 9,771,403.

(60) Provisional application No. 61/913,838, filed on Dec. 9, 2013, provisional application No. 61/943,884, filed on Feb. 24, 2014.

(51) Int. Cl.
  *C07K 14/47* (2006.01)
  *A61K 48/00* (2006.01)
  *C12N 9/22* (2006.01)
  *C12N 9/64* (2006.01)
  *C12N 15/86* (2006.01)

(52) U.S. Cl.
  CPC .......... *C07K 14/47* (2013.01); *C07K 14/4702* (2013.01); *C12N 9/22* (2013.01); *C12N 9/644* (2013.01); *C12N 15/86* (2013.01); *A61K 48/00* (2013.01); *C07K 2319/81* (2013.01); *C12N 2750/14133* (2013.01); *C12N 2750/14142* (2013.01); *C12N 2750/14143* (2013.01)

(58) Field of Classification Search
  None
  See application file for complete search history.

(56) References Cited

U.S. PATENT DOCUMENTS

| | | |
|---|---|---|
| 5,420,032 A | 5/1995 | Marshall et al. |
| 5,789,538 A | 8/1998 | Rebar et al. |
| 5,925,523 A | 7/1999 | Dove et al. |
| 6,007,988 A | 12/1999 | Choo |
| 6,013,453 A | 1/2000 | Choo |
| 6,140,081 A | 10/2000 | Barbas |
| 6,140,466 A | 10/2000 | Barbas, III et al. |
| 6,200,560 B1 | 3/2001 | Couto et al. |
| 6,200,759 B1 | 3/2001 | Dove et al. |
| 6,242,568 B1 | 6/2001 | Barbas, III et al. |
| 6,410,248 B1 | 6/2002 | Greisman et al. |
| 6,453,242 B1 | 9/2002 | Eisenberg et al. |
| 6,479,626 B1 | 11/2002 | Kim et al. |
| 6,503,717 B2 | 1/2003 | Case et al. |
| 6,534,261 B1 | 3/2003 | Cox, III et al. |
| 6,599,692 B1 | 7/2003 | Case et al. |
| 6,607,882 B1 | 8/2003 | Cox, III et al. |
| 6,642,028 B1 | 11/2003 | Ill et al. |
| 6,689,558 B2 | 2/2004 | Case |
| 6,794,136 B1 | 9/2004 | Eisenberg et al. |
| 6,824,978 B1 | 11/2004 | Cox, III et al. |
| 6,833,252 B1 | 12/2004 | Dujon et al. |
| 6,903,185 B2 | 6/2005 | Kim et al. |
| 6,933,113 B2 | 8/2005 | Case et al. |
| 6,936,243 B2 | 8/2005 | Snyder et al. |
| 6,979,539 B2 | 12/2005 | Cox, III et al. |
| 7,013,219 B2 | 3/2006 | Case et al. |
| 7,030,215 B2 | 4/2006 | Liu et al. |
| 7,067,317 B2 | 6/2006 | Rebar et al. |
| 7,070,934 B2 | 7/2006 | Cox, III et al. |
| 7,074,596 B2 | 7/2006 | Darzynkiewicz et al. |
| 7,153,949 B2 | 12/2006 | Kim et al. |
| 7,163,824 B2 | 1/2007 | Cox, III et al. |
| 7,238,346 B2 | 7/2007 | Vandendriessche et al. |
| 7,253,273 B2 | 8/2007 | Collingwood |
| 7,262,054 B2 | 8/2007 | Jamieson et al. |
| 7,361,635 B2 | 4/2008 | Miller et al. |
| 7,888,121 B2 | 2/2011 | Umov et al. |
| 7,914,796 B2 | 3/2011 | Miller et al. |
| 7,951,925 B2 | 5/2011 | Ando et al. |
| 7,972,843 B2 | 7/2011 | Hoffmann |
| 7,972,854 B2 | 7/2011 | Miller et al. |
| 8,034,598 B2 | 10/2011 | Miller |
| 8,110,379 B2 | 2/2012 | DeKeiver et al. |
| 8,129,510 B2 | 3/2012 | Kay et al. |
| 8,153,773 B2 | 4/2012 | Jemiielity et al. |
| 8,409,861 B2 | 4/2013 | Guschin et al. |
| 8,586,526 B2 | 11/2013 | Gregory et al. |
| 8,623,618 B2 | 1/2014 | Doyon et al. |
| 9,771,403 B2 | 9/2017 | Miller et al. |
| 9,971,403 B1* | 5/2018 | Kallmeyer ............ G06F 3/0346 |
| 10,407,476 B2* | 9/2019 | Miller ................. C07K 14/4702 |
| 10,968,261 B2* | 4/2021 | Miller ...................... C12N 9/644 |
| 10,975,375 B2* | 4/2021 | Rebar ...................... A61P 35/00 |

(Continued)

FOREIGN PATENT DOCUMENTS

| | | |
|---|---|---|
| CA | 2848417 A1 | 3/2013 |
| EP | 2 698 163 A1 | 2/2014 |
| GB | 2338237 A | 12/1999 |
| WO | WO-91/09122 | 6/1991 |

(Continued)

OTHER PUBLICATIONS

Wang, et al. (2000) "Sustained Expression of Therapeutic Level of Factor IX in Hemophilia B Dogs by AAV-Mediated Gene Therapy in Liver", Molecular Therapy, 1(2): 154-58. (Year: 2000).*

(Continued)

*Primary Examiner* — Robert M Kelly
(74) *Attorney, Agent, or Firm* — Foley & Lardner LLP

(57) ABSTRACT

Disclosed herein are methods and compositions for insertion of transgene sequences encoding proteins involved in clotting into the genome of a cell for treating conditions including hemophilias.

11 Claims, 8 Drawing Sheets

Specification includes a Sequence Listing.

(56) References Cited

U.S. PATENT DOCUMENTS

| | | |
|---|---|---|
| 2003/0134318 A1 | 7/2003 | Case et al. |
| 2003/0232410 A1 | 12/2003 | Liljedahl et al. |
| 2005/0026157 A1 | 2/2005 | Baltimore et al. |
| 2005/0064474 A1 | 3/2005 | Umov et al. |
| 2005/0208489 A1 | 9/2005 | Carroll et al. |
| 2005/0267061 A1 | 12/2005 | Martin |
| 2006/0063231 A1 | 3/2006 | Li et al. |
| 2006/0188987 A1 | 8/2006 | Guschin et al. |
| 2007/0117128 A1 | 5/2007 | Smith et al. |
| 2007/0218528 A1 | 9/2007 | Miller |
| 2008/0131962 A1 | 6/2008 | Miller |
| 2008/0159996 A1 | 7/2008 | Ando et al. |
| 2009/0029468 A1 | 1/2009 | Barbas et al. |
| 2009/0068164 A1 | 4/2009 | Segal et al. |
| 2009/0305346 A1 | 12/2009 | Gregory et al. |
| 2010/0041028 A1 | 2/2010 | Barbas et al. |
| 2010/0047805 A1 | 2/2010 | Wang |
| 2010/0065123 A1 | 3/2010 | Gust et al. |
| 2010/0218264 A1 | 8/2010 | Cui et al. |
| 2011/0027235 A1 | 2/2011 | Gregoty et al. |
| 2011/0184049 A1 | 7/2011 | Chuah et al. |
| 2011/0201055 A1 | 8/2011 | Doyon et al. |
| 2011/0207221 A1 | 8/2011 | Cost et al. |
| 2011/0265198 A1 | 10/2011 | Gregory et al. |
| 2011/0281361 A1 | 11/2011 | DeKelver et al. |
| 2012/0017290 A1 | 1/2012 | Cui et al. |
| 2012/0128635 A1† | 5/2012 | Gregory |
| 2012/0142062 A1 | 6/2012 | Doyon et al. |
| 2012/0195936 A1 | 8/2012 | Rudolph et al. |
| 2013/0122591 A1 | 5/2013 | Cost et al. |
| 2013/0137104 A1 | 5/2013 | Cost et al. |
| 2013/0177960 A1 | 7/2013 | Rebar |
| 2013/0177983 A1 | 7/2013 | Rebar |
| 2013/0183368 A1 | 7/2013 | Hutchison et al. |
| 2014/0017212 A1 | 1/2014 | Rebar |
| 2014/0112896 A1 | 4/2014 | Rebar |
| 2015/0056705 A1 | 2/2015 | Conway et al. |
| 2016/0237455 A1† | 8/2016 | Glucksmann |

FOREIGN PATENT DOCUMENTS

| | | |
|---|---|---|
| WO | WO 95/19431 A1 | 7/1995 |
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |
| WO | WO-01/40798 A2 | 6/2001 |
| WO | WO 01/60970 A2 | 8/2001 |
| WO | WO 01/88197 A2 | 11/2001 |
| WO | WO 02/016536 A1 | 2/2002 |
| WO | WO 02/077227 A2 | 10/2002 |
| WO | WO 02/099084 A2 | 12/2002 |
| WO | WO 03/016496 A2 | 2/2003 |
| WO | WO 07/014275 A2 | 2/2007 |
| WO | WO 09/042163 A2 | 4/2009 |
| WO | WO 09/054985 A1 | 4/2009 |
| WO | WO-2009/130208 A1 | 10/2009 |
| WO | WO 10/079430 A1 | 7/2010 |
| WO | WO 2013/044008 A2 | 3/2013 |
| WO | WO 2013/130807 A1 | 9/2013 |
| WO | WO 2013/169802 A1 | 11/2013 |
| WO | WO-2013/186563 A2 | 12/2013 |
| WO | WO-2014/064277 A1 | 5/2014 |

OTHER PUBLICATIONS

Anguela, et al., "In Vivo Genome Editing of Liver Albumin for Therapeutic Gene Expression Rescue of Hemophilic Mice Via Integration of Factor 9," Blood, 120(21):751 (2012).

Sun, et al., "Correction of Glycogen Storage Disease Type II By an Adeno-Associated Virus Vector Containing a Muscle-Specific Promotor," Molecular Therapy, 11(6):889-898 (2005).

Alwin, et al., "Custom Zinc-Finger Nucleases for Use in Human Cells," Molecular Therapy 12:610-617 (2005).

Anguela, et al., "Robust ZFN-Mediated Genome Editing in Adult Hemophilic Mice," Blood 122(19):3283-3287 (2013).

Argast, et al., "I-PPOL and I-CREL Homing Site Sequence Degeneracy Determined By Random Mutagenesis and Sequential In Vitro Enrichment," J. Mol. Biol. 280:345-353 (1998).

Beerli, et al., "Engineering Polydactyl Zinc-Finger Transcription Factors," Nature Biotechnol. 20:135-141(2002).

Belfort, et al., "Homing Endonucleases: Keeping the House in Order," Nucleic Acids Research 25:3379-3388 (1997).

Beurdeley, et al., "Compact Designer Talens for Efficient Genome Engineering," Nature Communications 4:1762 (2013) doi:10.10.38/ncomms2782.

Bhakta, et al., "The Generation of Zinc Finger Proteins By Modular Assembly," Methods Mol Biol, 649:3-30 (2010).

Boch, et al., "Breaking the Code of Dna Binding Specificity of TAL-Type III Effectors," Science 326:1509-1512 (2009).

Boissel, et al., "Megatals: a Rare-Cleaving Nuclease Architecture for Therapeutic Genome Engineering," Nucl. Acid Res. 1-13 (2013) doi: 10.1093/nar/gkt1224.

Bonas, et al., "Genetic and Structural Characterization of the a Virulence Gene AVRBS3 From Xanthomonas Campestris PV. Vesicatoria," Mol. Gen. Genet. 218:127-136 (1989).

Choo, et al., "Advances in Zinc Finger Engineering," Curr. Opin. Struct. Biol. 10:411-416(2000).

Dujon, et al., "Mobile Introns: Definition of Terms and Recommended Nomenclature," Gene 82:115-118 (1989).

Gimble, et al., "Substrate Recognition and Induced DNA Distortion By the PI-SCEI Endonuclease, An Enzyme Generated By Protein Splicing," J. Mol. Biol. 263:163-180 (1996).

Graham, et al., Performance of AAV8 Vectors Expressing Human Factor IX From a Hepatic-Selective Promoter Following Intravenous Injection Into Rats, Genet. Vaccines Ther. 6:9 (2008).

Guo, et al., "Directed Evolution of an Enhanced and Highly Efficient FOKI Cleavage Domain for Zinc Finger Nucleases," J. Mol. Biol. 400(1):96-107 (2010).

Guschin, et al., "A Rapid and General Assay for Monitoring Endogenous Gene Modification," Methods Mol. Biol. 649:247-256 (2010).

Haft, et al., "A Guild Of 45 CRISPR-Associated (CAS) Protein Families and Multiple CRISPR/CAS Subtypes Exist in Prokaryotic Genomes," PLoS Comput. Biol. 1(6):474-483 (2005).

Heuer, et al., "Repeat Domain Diversity of AVRBS3-LIKE Genes in Ralstonia Solanacearum Strains and Association With Host Preferences in the Field," Appl. And Envir. Micro. 73(13):4379-4384 (2007).

Isalan, et al., "A Rapid, Generally Applicable Method to Engineer Zinc Fingers Illustrated By Targeting the HIV-1 Promoter," Nat. Biotechnol. 19:656-660 (2001).

Jacotot, et al., "Therapeutic Peptides: Targeting the Mitochondrion To Modulate Apoptosis," Biochim. Biophys. Acta Bioenerg. 1757:1312-1323 (2006).

Jansen, et al., "Identification of Genes That Are Associated With DNA Repeats in Prokaryotes," Molecular Microbiology 43(6):1565-1575 (2002).

Karkan, et al., "A Unique Carrier for Delivery of Therapeutic Compounds Beyond the Blood-Brain Barrier," PLOS One DOI:10.1371/journal.pone.0002469 (2008).

Kay, et al., "A Bacterial Effector Acts as a Plant Transcription Factor and Induces a Cell Size Regulator," Science 318:648-651 (2007).

Kormann, et al., "Expression of Therapeutic Proteins After Delivery of Chemically Modified MRNA in Mice," Nature Biotechnology 29(2):154-157 (2011).

Lee, et al., "A New Potent HFIX Plasmid for Hemophilia B Gene Therapy," Pharm. Res. 7:1229-1232 (2004).

Levinson, et al., "A Transcribed Gene in an Intron of the Human Factor VIII Gene," Genomics 7(1):1-11 (1990).

Li, et al., "In Vivo Genome Editing Restores Haemostasis in a Mouse Model of Haemophilia," Nature 475(7355):217-221 (2011).

(56) References Cited

OTHER PUBLICATIONS

Makarova, et al., "A DNA Repair System Specific for Thermophilic Archaea and Bacteria Predicted By Genomic Context Analysis," *Nucleic Acids Res.* 30:482-496 (2002).
Makarova, et al., "A Putative Rna-Interference-Based Immune System in Prokaryotes: Computational Analysis of the Predicted Enzymatic Machinery, Functional Analogies With Eukaryotic RNAI, and Hypothetical Mechanisms of Action," *Biol. Direct* 1:7 (2006).
Mandell, et al., "Zinc Finger Tools: Custom DNA-Binding Domains for Transcription Factors and Nucleases," *Nucleic Acids Research* 34:W516-W523 (2006).
Manno, et al., "AAV-Mediated Factor IX Gene Transfer to Skeletal Muscle in Patients With Severe Hemophilia B," *Blood* 101(8):2963-2972 (2003).
Manno, et al., "Successful Transduction of Liver in Hemophilia By AAV—Factor IX and Limitations Imposed By the Host Immune Response," *Nature Medicine* 12(3):342-347 (2006).
Markusic, et al., "Effective Gene Therapy for Haemophilic Mice With Pathogenic Factor IX Antibodies," *EMBO Mol. Med.* 5:1698-1709 (2013).
McIntosh, et al., "Therapeutic Levels of FVIII Following a Single Peripheral Vein Administration of RAAV Vector Encoding a Novel Human Factor VIII Variant," *Blood* 121(17):3335-3344 (2013).
Miao, et al., "Inclusion of the Hepatic Locus Control Region, An Intron, and Untranslated Region Increases and Stabilizes Hepatic Factor IX Gene Expression In Vivo but Not In Vitro," *Molecular Therapy* 1(6):522-532 (2000).
Moscou, et al., "A Simple Cipher Governs DNA Recognition By TAL Effectors," *Science* 326:1501 (2009).
Nathwani, et al., "Adenovirus-Associated Virus Vector-Mediated Gene Transfer in Hemophilia B," *N. Engl. J. Med.* 365(25):2357-2365 (2011).
Nathwani et al., "Long-Term Safety and Efficacy Following Systemic Administration of a Self-Complementary AAV Vector Encoding Human Fix Pseudotyped With Serotype 5 and 8 CAPSID Proteins," *Molecular Therapy* 19(5):876-885 (2011).
Pabo, et al., "Design and Selection of Novel CYS2HIS2 Zinc Finger Proteins," *Ann. Rev. Biochem.* 70:313-340 (2001).
Perez, et al., "Establishment of HIV-1 Resistance in CD4+ T Cells By Genome Editing Using Zinc-Finger Nucleases," *Nat. Biotechnol.* 26:808-816 (2008).
Perler, et al., "Protein Splicing Elements: Inteins and Exteins a Definition of Terms and Recommended Nomenclature," *Nucleic Acids Research* 22:1125-1127 (1994).
Sharma, et al., "In Vivo Genome Editing of the Albumin Locus as a Platform for Protein Replacement Therapy," Gene Therapy, 126(15):1777-84 (2006).
Schomack, et al., "Gene-For-Gene-Mediated Recognition of Nuclear-Targeted AVRBS3-LIKE Bacterial Effector Proteins," *J. Plant Physiol.* 163(3):256-272 (2006).
Scott & Lozier, "Gene Therapy for Haemophilia: Prospects and Challenges to Prevent or Reverse Inhibitor Formation," *Br. J. Haematol.* 156(3):295-302 (2012).
Segal, et al., "Custom DNA-Binding Proteins Come of Age: Polydactyl Zinc-Finger Proteins," *Curr. Opin. Biotechnol.* 12:632-637 (2001).
Sharma, et al. "In Vivo Genome Editing of the Albumin Locus as a Platform for Protein Replacement Therapy," *Blood* 126(15):1777-84 (2015).
Sheng, et al., "Structure-Based Cleavage Mechanism of Thermus Thermophttus Argonaute DNA Guide Strand-Mediated DNA Target Cleavage," *Proc. Natl. Acad. Sci. USA* 111(2):652-657 (2013) doi: 10.1073/pnas.1321032111.
Shi, et al., "Lentivirus-Mediated Platelet-Derived Factor VIII Gene Therapy in Murine Haemophilia A," *J. Thromb Haemost.* 5(2):352-361 (2007).
Swarts, et al., "DNA-Guided DNA Interference By a Prokaryotic Argonaute," *Nature* 507(7491):258-261 (2014).
Miao et al., "Bioengineering of Coagulation Factor VIII for Improved Secretion," Blood, May 1, 2004, vol. 103, No. 9 (pp. 3412-3419).
Vandenriessche et al., "Gene therapy for the hemophilias," Journal of Thrombosis and Haemostasis, 2003, vol. 1 (pp. 1550-1558).
Wu et al., "Optimization of self-complementary AAV vectors for liver-directed expression results in sustained correction of hemophilia B at low vector dose," Molecular Therapy, Feb. 2008, vol. 16, No. 2 (pp. 280-289).
Anguela et al., "In Vivo Genome Editing of Liver Albumin for Therapeutic Gene Expression: Rescue of Hemophilic Mice Via Integration of Factor 9," Blood, 120(21):751, Nov. 16, 2012.†
Sun et al., "Correction of Glycogen Storage Disease Type II by an Adeno-associated Virus Vector Containing a Muscle-Specific Promoter," Mol. Ther., 11(6):889-898, 2005.†

\* cited by examiner
† cited by third party

FIG. 1

SB-42906 (AAV2/6 left ZFN)

| ITR | Promotor<br>ApoE/hAAT | NLS | ZFP<br>42906 | FokI<br>FokI-ELD | poly A | ITR |

SB-43043 (AAV2/6 right ZFN)

| ITR | Promotor<br>ApoE/hAAT | NLS | ZFP<br>43043 | FokI<br>FokI-KKR | poly A | ITR |

SB-F9 donor

| ITR | hALB Homology<br>LA | hF9 Transgene<br>SA | hF9 Exons 2-8 | hALB Homology<br>poly A | RA | ITR |

FIG. 6A

MAERPFQCRICMRNFSQSGNLARHIRTHTGEKPFQCRICMRKFAWADNLQNHTKIHTGEKPFQCRICMRNFSTSGNLTRHIRTHTGEKPFACDICGRKFAQSHLCLHTKIHLRGSQLVKSEEKKSELRHKLKYVPHEYIEIEIARNSTQDRILEMKVMEFFMKVYGRYGKHLGGSRKPDGAIYTVGSPIDYGVIVDTKAYSGGYNLPIGQADEMERYVEENQTRDKHLNPNEMWKVYPSSVTEFKLFVSGHFKGNYKAQLTRLNHITNCNGAVLSVEELLIGGEMIKAGTLTLEEVRRKFNNGEINFRS

FIG. 6B

METAPKKKRKVGIHGVPAAMETAERPFQCRICMETRNFSTPQLLDRHIRTHTGEKPFACDICGRKFALKWNLRTHTGEKPFQCRICMETRNFSDQSNLRAHIRTHTGEKPFACDICGRKFARNFSLTMETHTKIHTGERGFQCRICMETRNFSLRHDLDRHIRTHTGEKPFACDICGRKFAHRSNLNKHTKIHLRGSQLVKSEEKKSELRHKLKYVPHEYIEIEIARNSTQDRILEMETKVMETEFFMKVYETKVYGRYGKHLGGSRKPDGAIYTVGSPIDYGVIVDTKAYSGGYNLPIGQADEMETQRYVKENQTRNKHINPNEMWKVYPSSVTEFKLFVSGHFKGNYKAQLTRLNRKTNCNGAVLSVEELLIGGEMETIKAGTLTLEEVRRKFNNGEINF

FIG. 6C

```
ctgcgcgctcgctcactgaggcgcccgggcaaagcccgggcgtcggggcctttggtcgccgcctcagtgagcgag
cgagcgcgcagagaggaggagtgtttaacgctagcgtcctgcgcctaagcttgagcggagttccaattgtactgtac
agaaccatgtcacatgtttaacgctagcgtgccgactcggtaaactaaaagttttagacatttagactgtcttacgctaa
tcacatgcgctgccggcgCTTTATTTCTATTTTGTATTTTAGTCATAAATGCTTACAAGGTTATCTTATTAATCATCTTAAAGAATTATTTTGGC
ATTTATTTCTAAAATGGCATAGTAATTGTTAGTGAAGATTCAAGGTTATCTTATTAATAAATTCAAACATCCTAGGTA
AAAAAAAAGGTCAGATAGGGTTGAAGATTGAATTCATAACTAACTTAAGGAAAGTGCAAAGTAACTTAGAGTGACTGTTTT
AACTTCACAGATAAGAAAACGCCAACAAAATCCTGAACCGGTACAAGCTCAGGCAAGTGGAAGAGTTCGTGCAGGCAA
TCTTGATCATGAAAACGCCAACAAAATCCTGAACCGGTACAAGCTCAGGCAAGTGGAAGAGTTCGTGCAGGCAA
CCTGGAAGCGGAGTGCATGGAACGCAGTGCAGTGCAGCTTCGCAGTGCCGAGTGTTCAGCGGAAGCCCGCCAGCAACAGCTA
CTGGAAGCAGTACGTGACGGCCCCTTCGCGAGTGCGAAGAACTGCAGCGGCAAGAACATCAAGAACGGCCTGCGAGCA
CGAGTGCTGGTCTGCCAAGAACAGCGGCCAGAACAAGTGTGCTCGTGACCCGGACCTACCGTGACCACGGCGTGTTCCCTGACGT
GTTCTGCAAGAACAGCGCGAACAAGGTGTGCTCGTGACCCGGACCTACCGTGACCACGGCGTGTTCCCTGACGT
GCCCGCGAGTGCGAACTCAACGGAGGCCAAGCACCAGTTCCCGAACGAGCACATCACCCAGTCCTTCAACGACTTCACCCGGGT
GGACTACGTCGAAAACCGCAGATCGCGCTGTCCGAGGCCAAGCTGGGTCCAGGATCATCACCCAGAACTACACCCCCGGCTC
GGTGGGGCGGAGACGAGAAGTGGATCGTCCACCGCCTGCTGCTGGAAGTTCGGCAGGGATCGTGAACGCGTGATCCGCCGACAA
AATCGAGGAACGAGAAGTGGATCGTCCACCGCCTGCTGCTGGAAGTTCGGCAGGGATCGTGAACGCGTGATCCGCCGACAA
TATCAACCACCAGATATCGCCCTTTGCGAAGGGCATGGTCCTGCGGGTGCCCAGGGCAGCAAGGGCTACGCCAGGCGCCCT
GTACAACGTACACCAACATCTTTGCGAAGGGCATGGTCCTGCGGGTGCCCAGGGCAGCAAGGGCTACGCCAGGCGCCCT
AGAGTACTACACCAACATCTTTGCGAAGGGCATGGTCCTGCGGGTGCCCAGGGCAGCAAGGGCTACGCCAGGCGCCCT
GGTGCTGCAGTACCGGCTTCCACGAACGGCCAGTTCGAAGTTGCCCGGGGCCACAAGGCCAAGTTCAACCTCACCCAGAGTTCCGCAGGCGCCCT
CTGCCGCCGGTCGACCGGCATCATCGACGAAAACCAAGCCGAGTTGACCTGACCACCTACCGGAATGCGCCAGGCAAGTGCTCGAGAGTCGCAAGGGCCAGAATGCCCACGTACACTACCTAAGGTGTCAAGATACGT
GAACTGGATCAAAGAGAAACCAAGCCGACCTGAgtttaaactgtgccttctagttgccttctagttgtttgccccttgtgttt gccccc
cgtgccttcttgacctgaaagtgccactgtgccaactccactgccaaatgaaaattgcatgtgctgtcgatgtag
gtgtcattctatctgggggtggggtggtgccagagcaaggggaggattggaagacaagaaacatgcatagtagcaggcatgctgggatgc
ggggctctatggCTATCCATTGCATTTTAGTCTCTGTCTggataacacccccactgccgttagcgttttaaactgaaa
ACTTGTATTATTATTTATTTTCATTTTAGTCTCTGTCTggataacacccccactgccgttagcgttttaaactgaaa
ggcttagcaaacgcgtctccaacgtttcgcgttaacacccccactaataatcgagtgagtgtcttagtagtccgggtgttaacttaaa
gataactcgagcgcccgaccggctttgcccggacccggtgatgagttggccactcccctctcgcgtccgctcactactggagccgggacc
aaagtgccgacccgggctttgcccggacccggtgatgagttggccactcccctctcgcgtccgctcactactggagccgggacc
aaagtgccgacccgggctttgcccggacccggtgatgagttggccactcccctctcgcgtccgctcactactggagccgggacc
aaagtgccgacccgggctttgcccggacccggtgatgagttggccactcccctctcgcgtccgctcactactggagccgggacc
```

METHODS AND COMPOSITIONS FOR TREATING HEMOPHILIA

CROSS-REFERENCE TO RELATED APPLICATIONS

The present application is a continuation of U.S. patent application Ser. No. 15/673,163, filed Aug. 9, 2017, now U.S. Pat. No. 10,407,476, which is a continuation of U.S. patent application Ser. No. 14/564,722, filed Dec. 9, 2014, now U.S. Pat. No. 9,771,403, which claims the benefit of U.S. Provisional Application No. 61/913,838, filed Dec. 9, 2013 and U.S. Provisional Application No. 61/943,884, filed Feb. 24, 2014, the disclosures of which are hereby incorporated by reference in its entirety.

SEQUENCE LISTING

The instant application contains a Sequence Listing which has been submitted electronically in ASCII format and is hereby incorporated by reference in its entirety. Said ASCII copy, created on Jun. 26, 2019 is named 83250115US5SL.txt and is 13,401 bytes in size.

STATEMENT OF RIGHTS TO INVENTIONS MADE UNDER FEDERALLY SPONSORED RESEARCH

Not applicable.

TECHNICAL FIELD

The present disclosure is in the fields of gene modification and treatment of hemophilia.

BACKGROUND

Hemophilias such as hemophilia A and hemophilia B, are genetic disorders of the blood-clotting system, characterized by bleeding into joints and soft tissues, and by excessive bleeding into any site experiencing trauma or undergoing surgery. Hemophilia A is clinically indistinguishable from hemophilia B, but Factor VIII (FVIII or F8) is deficient or absent in hemophilia A while Factor IX (FIX or F.IX) is deficient or absent in patients with hemophilia B. The Factor VIII gene encodes a plasma glycoprotein that circulates in association with von Wilebrand's factor in its inactive form. Upon surface injury, the intrinsic clotting cascade initiates and factor VIII is released from the complex and becomes activated. The activated form acts with Factor IX to activate Factor X to become the activated Xa, eventually leading to change of fibrinogen to fibrin and clot induction. See, Levinson et al. (1990) *Genomics* 7(1):1-11. 40-50% of hemophilia A patients have a chromosomal inversion involving Factor VIII intron 22 (also known as IVS22). The inversion is caused by an intra-chromosomal recombination event between a 9.6 kb sequence within the intron 22 of the Factor VIII gene and one of the two closely related inversely orientated sequences located about 300 kb distal to the Factor VIII gene, resulting in an inversion of exons 1 to 22 with respect to exons 23 to 26. See, Textbook of Hemophilia, Lee et al. (eds) 2005, Blackwell Publishing. Other hemophilia A patients have defects in Factor VIII including active site mutations, and nonsense and missense mutations. For its part, Factor IX (F.IX or FIX) encodes one of the serine proteases involved with the coagulation system, and it has been shown that restoration of even 3% of normal circulating levels of wild type Factor IX protein can prevent spontaneous bleeding. Additional hemophilias are associated with aberrant expression of other clotting factors. For example, Factor VII deficiency is an autosomal recessive trait occurring in approximately 1 in 300,000 to 500,000 people and is associated with inadequate Factor VII levels in the patient. Similarly, Factor X deficiency is also an autosomal recessive trait occurring in 1 in every 500,000 to 1 million people, and is caused by genetic variants of the FX gene. Factor X deficiency can have varying degrees of severity in the patient population.

Current treatments for Hemophilia B rely on chronic, repeated intravenous infusions of purified recombinant Factor IX and suffer from a number of drawbacks. This includes the need for repeated intravenous infusions, is associated with inhibitor formation, and is prophylactic rather than curative.

Gene therapy for patients with Hemophilia A or B, involving the introduction of plasmid and other vectors (e.g., AAV) encoding a functional Factor VIII or Factor IX proteins have been described. See, e.g., U.S. Pat. Nos. 6,936,243; 7,238,346; and 6,200,560; Shi et al. (2007) *J Thromb Haemost.* (2):352-61; Lee et al. (2004) *Pharm. Res.* 7:1229-1232; Graham et al. (2008) *Genet Vaccines Ther.* 3:6-9; Manno et al. (2003) *Blood* 101(8): 2963-72; Manno et al. (2006) *Nature Medicine* 12(3): 342-7; Nathwani et al. (2011) *Molecular Therapy* 19(5): 876-85; Nathwani et al. (2011); *N Engl J Med.* 365(25): 2357-65. However, in these protocols, the formation of inhibitory anti-factor VIII or IX (anti-F8 or anti-FIX) antibodies and antibodies against the delivery vehicle remains a major complication of Factor VIII and Factor IX replacement-based treatment for hemophilia. See, e.g., Scott & Lozier (2012) *Br J Haematol.* 156(3):295-302.

Various methods and compositions for targeted cleavage of genomic DNA have been described. Such targeted cleavage events can be used, for example, to induce targeted mutagenesis, induce targeted deletions of cellular DNA sequences, and facilitate targeted recombination at a predetermined chromosomal locus. See, e.g., U.S. Pat. Nos. 8,623,618; 8,034,598; 8,586,526; 6,534,261; 6,599,692; 6,503,717; 6,689,558; 7,067,317; 7,262,054; 7,888,121; 7,972,854; 7,914,796; 7,951,925; 8,110,379; 8,409,861; U.S. Patent Publication Nos. 2003/0232410; 2005/0208489; 2005/0026157; 2006/0063231; 2008/0159996; 2010/00218264; 2012/0017290; 2011/0265198; 2013/0137104; 2013/0122591; 2013/0177983; 2013/0177960 and 2015/0056705, the disclosures of which are incorporated by reference in their entireties for all purposes. These methods often involve the use of engineered cleavage systems to induce a double strand break (DSB) or a nick in a target DNA sequence such that repair of the break by an error born process such as non-homologous end joining (NHEJ) or repair using a repair template (homology directed repair or HDR) can result in the knock out of a gene or the insertion of a sequence of interest (targeted integration). This technique can also be used to introduce site specific changes in the genome sequence through use of a donor oligonucleotide, including the introduction of specific deletions of genomic regions, or of specific point mutations or localized alterations (also known as gene correction). Cleavage can occur through the use of specific nucleases such as engineered zinc finger nucleases (ZFN), transcription-activator like effector nucleases (TALENs), or using the CRISPR/Cas system with an engineered crRNA/tracr RNA (single guide RNA') to guide specific cleavage. Further, targeted nucleases are being developed based on the Argonaute system (e.g., from *T. thermophilus*, known as 'TtAgo', see Swarts et al. (2014) *Nature* 507(7491): 258-261), which also may have the potential for uses in genome editing and gene therapy.

This nuclease-mediated targeted transgene insertion approach offers the prospect of improved transgene expression, increased safety and expressional durability, as compared to classic integration approaches, since it allows exact transgene positioning for a minimal risk of gene silencing or activation of nearby oncogenes.

Targeted integration of a transgene may be into its cognate locus, for example, insertion of a wild type transgene into the endogenous locus to correct a mutant gene. Alternatively, the transgene may be inserted into a non-cognate locus, for example a "safe harbor" locus. Several safe harbor loci have been described, including CCR5, HPRT, AAVS1, Rosa and albumin. See, e.g., U.S. Pat. Nos. 7,951,925 and 8,110,379; U.S. Patent Publication Nos. 2008/0159996; 2010/00218264; 2012/0017290; 2011/0265198; 2013/0137104; 2013/0122591; 2013/0177983, 2013/0177960 and 2015/0056705. For example, U.S. Patent Publication No. 2011/0027235 relates to targeted integration of functional proteins into isolated stem cells and U.S. Patent Publication No. 2012/0128635 describes methods of treating hemophilia B. See also Li et al. (2011) *Nature* 475 (7355):217-221 and Anguela et al. (2013) *Blood* 122:3283-3287.

However, there remains a need for additional compositions and methods of treating hemophilias.

SUMMARY

Disclosed herein are methods and compositions for targeted integration of a sequence encoding a protein, such as a functional clotting factor protein (e.g., Factor VII, Factor VIII, Factor IX, Factor X, and/or Factor XI). Expression of a functional Factor VIII ("F8") and/or Factor IX ("F.IX" or "FIX") protein can result, for example, in the treatment and/or prevention of hemophilia A (Factor VIII) and/or hemophilia B (Factor IX), while expression of a functional Factor VII or Factor X can treat or prevent hemophilias associated with Factor VII and/or Factor X deficiency. Nucleases, for example engineered meganucleases, zinc finger nucleases (ZFNs), TALE-nucleases (TALENs including fusions of TALE effectors domains with nuclease domains from restriction endonucleases and/or from meganucleases (such as mega TALEs and compact TALENs)), Ttago system and/or CRISPR/Cas nuclease systems are used to cleave DNA at a 'safe harbor' gene locus (e.g. CCR5, AAVS1, HPRT, Rosa or albumin) in the cell into which the gene is inserted. Targeted insertion of a donor transgene may be via homology directed repair (HDR) or non-homology repair mechanisms (e.g., NHEJ donor capture). The nuclease can induce a double-stranded (DSB) or single-stranded break (nick) in the target DNA. In some embodiments, two nickases are used to create a DSB by introducing two nicks. In some cases, the nickase is a ZFN, while in others, the nickase is a TALEN or a CRISPR/Cas nickase. In some embodiments, the methods and compositions involve at least one protein that binds to an albumin gene in a cell.

In one aspect, described herein is a non-naturally occurring zinc-finger protein (ZFP) that binds to a target site in a region of interest (e.g., an albumin gene) in a genome, wherein the ZFP comprises one or more engineered zinc-finger binding domains. In one embodiment, the ZFP is a zinc-finger nuclease (ZFN) that cleaves a target genomic region of interest, wherein the ZFN comprises one or more engineered zinc-finger binding domains and a nuclease cleavage domain or cleavage half-domain. Cleavage domains and cleavage half domains can be obtained, for example, from various restriction endonucleases and/or homing endonucleases. In one embodiment, the cleavage half-domains are derived from a Type IIS restriction endonuclease (e.g., FokI). In certain embodiments, the zinc finger domain recognizes a target site in an albumin gene, for example a zinc finger protein with the recognition helix domains ordered as shown in a single row of Table 1. In some embodiments, the zinc finger protein comprises five or six zinc finger domains designated and ordered F1 to F5 or F1 to F6, as shown in a single row of Table 1.

In another aspect, described herein is a Transcription Activator Like Effector (TALE) protein that binds to target site in a region of interest (e.g., an albumin gene) in a genome, wherein the TALE comprises one or more engineered TALE binding domains. In one embodiment, the TALE is a nuclease (TALEN) that cleaves a target genomic region of interest, wherein the TALEN comprises one or more engineered TALE DNA binding domains and a nuclease cleavage domain or cleavage half-domain. Cleavage domains and cleavage half domains can be obtained, for example, from various restriction endonucleases and/or homing endonucleases (meganuclease). In one embodiment, the cleavage half-domains are derived from a Type IIS restriction endonuclease (e.g., FokI). In other embodiments, the cleavage domain is derived from a meganuclease, which meganuclease domain may also exhibit DNA-binding functionality.

In another aspect, described herein is a CRISPR/Cas system that binds to target site in a region of interest (e.g., an albumin gene) in a genome, wherein the CRISPR/Cas system comprises one or more engineered single guide RNA or a functional equivalent, as well as a Cas9 nuclease.

The nucleases (e.g., ZFN, CRISPR/Cas system, Ttago and/or TALEN) as described herein may bind to and/or cleave the region of interest in a coding or non-coding region within or adjacent to the gene, such as, for example, a leader sequence, trailer sequence or intron, or within a non-transcribed region, either upstream or downstream of the coding region. In certain embodiments, the nuclease (e.g., ZFN) binds to and/or cleaves an albumin gene.

In another aspect, described herein is a polynucleotide encoding one or more nucleases (e.g., ZFNs, CRISPR/Cas systems, Ttago and/or TALENs described herein) or other proteins. The polynucleotide may be, for example, mRNA. In some aspects, the mRNA may be chemically modified (See e.g. Kormann et al. (2011) *Nature Biotechnology* 29(2):154-157). In other aspects, the mRNA may comprise an ARCA cap (see U.S. Pat. Nos. 7,074,596 and 8,153,773). In further embodiments, the mRNA may comprise a mixture of unmodified and modified nucleotides (see U.S. Patent Publication No. 2012/0195936).

In another aspect, described herein is an expression vector (e.g., a ZFN, CRISPR/Cas system, Ttago and/or TALEN expression vector) comprising a polynucleotide, encoding one or more proteins including nucleases (e.g., ZFNs, CRISPR/Cas systems, Ttago and/or TALENs) as described herein, operably linked to a promoter. In one embodiment, the expression vector is a viral vector. In one aspect, the viral vector exhibits tissue specific tropism.

In another aspect, described herein is a host cell comprising one or more expression vectors, including nuclease (e.g., ZFN, CRISPR/Cas systems, Ttago and/or TALEN) expression vectors.

In another aspect, pharmaceutical compositions comprising an expression vector as described herein are provided. In some embodiments, the pharmaceutical composition may comprise more than one expression vector. In some embodiments, the pharmaceutical composition comprises a first expression vector comprising a first polynucleotide, and a second expression vector comprising a second polynucleotide. In some embodiments, the first polynucleotide and the second polynucleotide are different. In some embodiments, the first polynucleotide and the second polynucleotide are substantially the same. The pharmaceutical composition may further comprise a donor sequence (e.g., a Factor IX donor sequence). In some embodiments, the donor sequence is associated with an expression vector.

In one aspect, the methods and compositions of the invention comprise genetically modified cells comprising a transgene expressing a functional version of a protein that is aberrantly expressed in a hemophilia (Factor VII, Factor VIII, Factor IX, Factor X, and/or Factor XI protein), in which the transgene is integrated into an endogenous safe-harbor gene (e.g., albumin gene) of the cell's genome. In certain embodiments, the transgene is integrated in a site-specific (targeted) manner using at least one nuclease. In certain embodiments, the nuclease (e.g., ZFNs, TALENs, Ttago and/or CRISPR/Cas systems) is specific for a safe harbor gene (e.g. CCR5, HPRT, AAVS1, Rosa or albumin. See, e.g., U.S. Pat. Nos. 7,951,925 and 8,110,379; U.S. Patent Publication Nos. 2008/0159996; 2010/0218264; 2012/0017290; 2011/0265198; 2013/0137104; 2013/0122591; 2013/0177983; 2013/0177960; and 2015/0056705. In some embodiments, the safe harbor is an albumin gene.

In another aspect, described herein is a method of genetically modifying a cell, in vitro and/or in vivo, to produce Factor VII, Factor VIII, Factor IX, Factor X and/or Factor XI, the method comprising cleaving an endogenous safe harbor gene in the cell using one or more nucleases (e.g., ZFNs, TALENs, CRISPR/Cas) such that a transgene encoding Factor VII, Factor VIII, Factor IX, Factor X and/or Factor XI is integrated into the safe harbor locus and expressed in the cell. In certain embodiments, the safe harbor gene is a CCR5, HPRT, AAVS1, Rosa or albumin gene. In certain embodiments, the cell is a mammalian cell. In certain embodiments, the cell is a primate cell. In certain embodiments, the cell is a human cell. In one set of embodiments, methods for cleaving an albumin gene in a cell (e.g., a liver cell) are provided comprising introducing, into the cell, one or more expression vectors disclosed herein under conditions such that the one or more proteins are expressed and the albumin gene is cleaved. The albumin gene may be modified, for example, by integration of a donor sequence into the cleaved albumin gene.

In certain embodiments, the method comprises genetically modifying a cell to produce Factor IX, the method comprising administering to the cell the zinc finger nucleases (ZFNs) shown in Table 1 (or polynucleotides encoding these ZFNs) and a donor encoding a Factor IX protein. The ZFNs and donor may be on the same or different vectors in any combination, for example on 3 separate AAV vectors each carrying one of the components; one vector carrying two of the components and a separate vector carrying the 3$^{rd}$ component; or one vector carrying all 3 components.

In another aspect, provided herein are methods for providing a functional protein (e.g., Factor VIII) lacking or deficient in a mammal, or in a primate, such as a human primate, such as a human patient with hemophilia A, for example for treating hemophilia A. In some cases, the functional protein is a circulating plasma protein. In some cases, the functional protein is a non-circulating plasma protein. In some cases, the functional protein may be liver specific. In another aspect, provided herein are methods for providing a functional protein (e.g., Factor IX) lacking or deficient in a mammal, or in a primate, such as a human primate, such as a human patient with hemophilia B, for example for treating hemophilia B. In another aspect, provided herein are methods for providing a functional protein (e.g. Factor VII) to a mammal, or in a primate, such as a human primate, such as a human patient, for treating hemophilia associated with Factor VII deficiency. In another aspect, provided herein are methods for providing a functional protein (e.g. Factor X) for treating hemophilia associated with Factor X deficiency. In another aspect, provided herein are methods for providing a functional protein (e.g. Factor XI) for treating hemophilia associated with Factor XI deficiency. In certain embodiments, the methods comprise using nucleases to integrate a sequence encoding a functional Factor VII, Factor VIII, Factor IX, Factor X, and/or Factor XI protein in a cell in a subject in need thereof. In other embodiments, the method comprises administering a genetically modified cell (expressing a functional version of a protein that is aberrantly expressed in a subject with hemophilia) to the subject. Thus, an isolated cell may be introduced into the subject (ex vivo cell therapy) or a cell may be modified when it is part of the subject (in vivo). Also provided is the use of the donors and/or nucleases described herein for the treatment of a hemophilia (e.g., hemophilia A with Factor VIII donor, hemophilia B with Factor IX donor, Factor VII deficiency with Factor VII, Factor X deficiency with Factor X and/or Factor XI deficiency with Factor XI), for example, in the preparation of medicament for treatment of hemophilia. In certain embodiments, the Factor VIII protein comprises a B-domain deletion. In certain embodiments, the Factor VIII- and/or Factor IX-encoding sequence is delivered using a viral vector, a non-viral vector (e.g., plasmid) and/or combinations thereof.

In any of the compositions and methods described, the nuclease(s) and/or transgene(s) may be carried on an AAV vector, including but not limited to AAV1, AAV3, AAV4, AAV5, AAV6, AAV8, AAV9 and AAVrh10 or pseudotyped AAV such as AAV2/8, AAV8.2, AAV2/5 and AAV2/6 and the like. In some embodiments, the AAV vector is an AAV2/6 vector. In certain embodiments, the nucleases and transgene donors are delivered using the same AAV vector types. In other embodiments, the nucleases and transgene donors are delivered using different AAV vector types. The nucleases and transgenes may be delivered using one or more vectors, for example, one vector carries both the transgene and nuclease(s); two vectors where one carries the nuclease(s) (e.g., left and right ZFNs of a ZFN pair, for example with a 2A peptide) and one carries the transgene; or three vectors where one vector carries one nuclease of a nuclease pair (e.g., left ZFN), a separate vector carries the other nuclease of a nuclease pair (e.g., right ZFN) and a third separate vector carries the transgene. See, FIG. 2. In embodiments in which two or more vectors or used, the vectors may be used at the same concentrations or in different ratios, for example, the transgene donor vector(s) may be administered at 2-fold, 3-fold, 4-fold, 5-fold or more higher concentrations than the nuclease vector(s). For example, a first nuclease, a second nuclease that is different from the first nuclease, and a transgene donor may be delivered in a ratio of about 1:1:1, about 1:1:2, about 1:1:3, about 1:1:4, about 1:1:5, about 1:1:6, about 1:1:7, about 1:1:8, about 1:1:9, about 1:1:10, about 1:1:11, about 1:1:12, about 1:1:13, about 1:1:14, about 1:1:15, about 1:1:16, about 1:1:17, about 1:1:18, about 1:1:19, or, in some cases, about 1:1:20. In an illustrative embodiment, a first nuclease, a second nuclease that is different from the first nuclease, and a transgene donor are delivered in a ratio of about 1:1:8. In certain embodiments, the nucleases and/or transgene donors are delivered via intravenous (e.g., intra-portal vein) administration into the liver of an intact animal.

In any of the compositions and methods described herein, the protein encoded by the transgene may comprise a Factor VIII protein, or a modified Factor VIII protein, for example a B-Domain Deleted Factor VIII (BDD-F8) or fragment thereof. In other embodiments, the protein encoded by the transgene comprises a Factor IX protein. In other embodiments, the protein encoded by the transgene comprises a Factor VII protein. In other embodiments, the protein encoded by the transgene comprises a Factor X protein. In any of the compositions or methods described herein, the transgene also comprises a transcriptional regulator while in others, it does not and transcription is regulated by an endogenous regulator. In another aspect, the methods of the invention comprise a composition for therapeutic treatment of a subject in need thereof. In some embodiments, the composition comprises engineered stem cells comprising a safe harbor specific nuclease, and a transgene donor encoding Factor VII, Factor VIII, Factor IX, Factor X and/or Factor XI protein or a functional fragment and/or truncation thereof. In other embodiments, the composition comprises engineered stem cells that have been modified and express a transgene donor encoding Factor VII, Factor VIII, Factor IX, Factor X, and/or Factor XI protein or a functional fragment and/or truncation thereof.

In any of the compositions or methods described herein, the cell may be a eukaryotic cell. Non-limiting examples of suitable cells include eukaryotic cells or cell lines such as secretory cells (e.g., liver cells, mucosal cells, salivary gland cells, pituitary cells, etc.), blood cells (red blood cells), red blood precursory cells, hepatic cells, muscle cells, stem cells (e.g., embryonic stem cells, induced pluripotent stem cells, hepatic stem cells, hematopoietic stem cells (e.g., CD34+)) or endothelial cells (e.g., vascular, glomerular, and tubular endothelial cells). Thus, the target cells may be primate cells, for example human cells, or the target cells may be mammalian cells, (including veterinary animals), for example especially nonhuman primates and mammals of the orders Rodenta (mice, rats, hamsters), Lagomorpha (rabbits), Carnivora (cats, dogs), and Arteriodactyla (cows, pigs, sheep, goats, horses). In some aspects, the target cells comprise a tissue (e.g. liver). In some aspects, the target cell is a stem cell (e.g., an embryonic stem cell, an induced pluripotent stem cell, a hepatic stem cell, etc.) or non-human animal embryo by any of the methods described herein, and then the embryo is implanted such that a live animal is born. The animal is then raised to sexual maturity and allowed to produce offspring wherein at least some of the offspring comprise the genomic modification. The cell can also comprise an embryo cell, for example, of a mouse, rat, rabbit or other mammal cell embryo. The cell may be from any organism, for example human, non-human primate, mouse, rat, rabbit, cat, dog or other mammalian cells. The cell may be isolated or may be part of an organism (e.g., subject).

In any of the methods and compositions described herein, the transgene may be integrated into the endogenous safe harbor gene such that some, all or none of the endogenous gene is expressed, for example a fusion protein with the integrated transgene. In some embodiments, the endogenous safe harbor gene is an albumin gene and the endogenous sequences are albumin sequences. The endogenous may be present on the amino (N)-terminal portion of the exogenous protein and/or on the carboxy (C)-terminal portion of the exogenous protein. The albumin sequences may include full-length wild-type or mutant albumin sequences or, alternatively, may include partial albumin amino acid sequences. In certain embodiments, the albumin sequences (full-length or partial) serve to increase the serum half-life of the polypeptide expressed by the transgene to which it is fused and/or as a carrier. In other embodiments, the transgene comprises albumin sequences and is targeted for insertion into another safe harbor within a genome. Furthermore, the transgene may include an exogenous promoter (e.g., constitutive or inducible promoter) that drives its expression or its expression may be driven by endogenous control sequences (e.g., endogenous albumin promoter). In some embodiments, the donor includes additional modifications, including but not limited to codon optimization, addition of glycosylation sites, truncations and the like.

In some embodiments, a fusion protein comprising a zinc finger protein and a wild-type or engineered cleavage domain or cleavage half-domain are provided.

In some embodiments, a pharmaceutical composition is provided comprising: (i) an AAV vector comprising a polynucleotide encoding a zinc finger nuclease, the zinc finger nuclease comprising a FokI cleavage domain and a zinc finger protein comprising 5 zinc finger domains ordered F1 to F5, wherein each zinc finger domain comprises a recognition helix region and wherein the recognition helix regions of the zinc finger protein are shown in the first row of Table 1 (SEQ ID NOs:4-8) (e.g., SEQ ID NO. 15); (ii) an AAV vector comprising a polynucleotide encoding a zinc finger nuclease, the zinc finger nuclease comprising a FokI cleavage domain and a zinc finger protein comprising 6 zinc finger domains ordered F1 to F6, wherein each zinc finger domain comprises a recognition helix region and wherein the recognition helix regions of the zinc finger protein are shown in the second row of Table 1 (SEQ ID NOs:9-14) (e.g., SEQ ID NO. 16); and (iii) an AAV vector comprising a donor encoding a Factor IX protein (e.g., SEQ ID NO. 17).

In some embodiments, (i), (ii), and (iii) are provided in a ratio about 1:1:1, about 1:1:2, about 1:1:3, about 1:1:4, about 1:1:5, about 1:1:6, about 1:1:7, about 1:1:8, about 1:1:9, about 1:1:10, about 1:1:11, about 1:1:12, about 1:1:13, about 1:1:14, about 1:1:15, about 1:1:16, about 1:1:17, about 1:1:18, about 1:1:19, or about 1:1:20.

In some embodiments, a pharmaceutical composition is provided comprising a first polynucleotide comprising or consisting of an amino acid sequence having 80%, 90%, 95%, 99%, 99.5% or 99.8% or more identity to SEQ ID NO. 15, a second polynucleotide comprising or consisting of an amino acid sequence having 80%, 90%, 95%, 99%, 99.5% or 99.8% or more identity to SEQ ID NO. 16, and, optionally, a donor sequence comprising or consisting of an amino acid sequence having 80%, 90%, 95%, 99%, 99.5% or 99.8% or more identity to SEQ ID NO. 17.

In some embodiments, a pharmaceutical composition is provided comprising or consisting of a first polynucleotide comprising a sequence as in SEQ ID NO. 15, a second polynucleotide comprising or consisting of a sequence as in SEQ ID NO. 16, and, optionally, a donor sequence comprising or consisting of a sequence as in SEQ ID NO. 17.

In any of the compositions or methods described herein, cleavage can occur through the use of specific nucleases such as engineered zinc finger nucleases (ZFN), transcription-activator like effector nucleases (TALENs), or using the Ttago or CRISPR/Cas system with an engineered crRNA/tracr RNA ('single guide RNA') to guide specific cleavage. In some embodiments, two nickases are used to create a DSB by introducing two nicks. In some cases, the nickase is a ZFN, while in others, the nickase is a TALEN or a CRISPR/Cas system. Targeted integration may occur via homology directed repair mechanisms (HDR) and/or via non-homology repair mechanisms (e.g., NHEJ donor capture). The nucleases as described herein may bind to and/or cleave the region of interest in a coding or non-coding region within or adjacent to the gene, such as, for example, a leader sequence, trailer sequence or intron, or within a non-transcribed region, either upstream or downstream of the coding region. In certain embodiments, the nuclease cleaves the target sequence at or near the binding site (e.g., the binding site shown in Table 1). Cleavage can result in modification of the gene, for example, via insertions, deletions or combinations thereof. In certain embodiments, the modification is at or near the nuclease(s) binding and/or cleavage site(s), for example, within 1-300 (or any value therebetween) base pairs upstream or downstream of the site(s) of cleavage, more preferably within 1-100 base pairs (or any value therebetween) of either side of the binding and/or cleavage site(s), even more preferably within 1 to 50 base pairs (or any value therebetween) on either side of the binding and/or cleavage site(s).

The methods and compositions described may be used to treat or prevent a hemophilia in a subject in need thereof. In some embodiments, a method of treating a patient with hemophilia B is provided comprising administering to the patient any expression vector or pharmaceutical composition described herein, wherein expression vector or pharmaceutical composition mediates targeted integration of a transgene encoding a functional Factor IX protein into an endogenous albumin gene. In some embodiments, the compositions comprise vectors and are used to target liver cells. In other embodiments, the compositions comprise engineered stem cells and are given to a patient as a bone marrow transplant. In some instances, patients are partially or completely immunoablated prior to transplantation. In other instances, patients are treated with one or more immunosuppressive agents before, during and/or after nuclease-mediated modification an endogenous gene (e.g., targeted integration of a FIX transgene into an albumin locus).

In other aspects, described herein are methods of treating and/or preventing Hemophilia B using a system ("SB-FIX" system) comprising engineered zinc finger nucleases (ZFNs) as shown in Table 1 to site-specifically integrate a corrective copy of the human Factor 9 (hF9) transgene into the genome of the subject's own hepatocytes in vivo. Integration of the hF9 transgene is targeted to intron 1 of the albumin locus, resulting in stable, high level, liver-specific expression and secretion of Factor IX in to the blood. SB-FIX contains three individual recombinant adeno-associated virus serotype 2/6 (rAAV2/6) vectors, administered as a serial and consecutive intravenous dose: a first vector (SB-42906 of Table 1) encoding SBS42906, a second vector (SB-43043) encoding SBS43043, and a third vector (SB-F9 donor, also referred to as "SB-FIX donor") providing a DNA repair template encoding a promoterless hF9 transgene. Delivery of all three vectors results in 1) specific and selective cleavage at a pre-defined site in intron 1 of the albumin locus by the pair of engineered sequence-specific ZFNs (SBS42906 & SBS43043) and 2) stable integration of the hF9 transgene coded by the DNA repair template at the site of the ZFN-induced DNA break. Placement of the hF9 transgene into the genome, and under the control of the highly expressed endogenous albumin locus provides permanent, liver-specific expression of Factor IX for the lifetime of the subject.

Furthermore, any of the methods described herein may further comprise additional steps, including partial hepatectomy or treatment with secondary agents that enhance transduction and/or induce hepatic cells to undergo cell cycling. Examples of secondary agents include gamma irradiation, UV irradiation, tritiated nucleotides such as thymidine, cis-platinum, etoposide, hydroxyurea, aphidicolin, prednisolone, carbon tetrachloride and/or adenovirus.

The methods described herein can be practiced in vitro, ex vivo or in vivo. In certain embodiments, the compositions are introduced into a live, intact mammal. The mammal may be at any stage of development at the time of delivery, e.g., embryonic, fetal, neonatal, infantile, juvenile or adult. Additionally, targeted cells may be healthy or diseased. In certain embodiments, one or more of the compositions are delivered intravenously (e.g., to the liver via the intraportal vein, for example tail vein injection), intra-arterially, intraperitoneally, intramuscularly, into liver parenchyma (e.g., via injection), into the hepatic artery (e.g., via injection), and/or through the biliary tree (e.g., via injection).

In one particular aspect, the methods and compositions described herein include a therapeutic composition comprising (i) a donor transgene coding for FVIII (ii) a nuclease (e.g., ZFN, TALENs, Ttago or CRISPR/Cas system) targeting a locus of an endogenous gene other than FVIII, respectively, for example, targeting the endogenous albumin gene of a mammal, or primate or human, such as hemophilia patient. In certain embodiments, the therapeutic composition comprises the FVIII donor transgene and the albumin gene-specific nuclease in separate, independent vectors, such as separate AAV vectors, in different amounts, which can be administered together (e.g., mixed into a single solution or administered simultaneously) or, alternatively, which can be administered separately (for example, administered in separate solutions with a substantial delay, e.g., 10 minutes or more, 30 minutes or more, 1 hour or more, 2 hours or more, 3 hours or more, or longer between respective administrations). In certain embodiments, the therapeutic composition is administered to provide integration of the FVIII donor transgene into the non-FVIII locus and subsequent expression of the integrated FVIII to achieve a therapeutic level of FVIII in the plasma of the mammal, or primate or human, or hemophilia patient. In certain embodiments, a therapeutic level of FVIII can include, for example, greater than 2%, greater than 4%, greater than 5%, greater than 6%, greater than 8%, greater than 10%, greater than 12%, greater than 15%, greater than 20%, greater than 25%, or more of a clinically-acceptable normal plasma concentration of FVIII. Alternatively or in addition, a therapeutic level of FVIII can include, for example, greater than 2%, greater than 4%, greater than 5%, greater than 6%, greater than 8%, greater than 10%, greater than 12%, greater than 15%, greater than 20%, greater than 25%, greater than 30%, greater than 35%, or more of the plasma concentration of functional FVIII measured in the individual mammal, or primate or human, or hemophilia patient prior to administration of the FVIII donor transgene and the albumin gene nuclease to that individual.

In another particular aspect, the methods and compositions described herein include a therapeutic composition comprising (i) a donor transgene coding for FIX (ii) a nuclease (e.g., ZFN, TALENs, Ttago or CRISPR/Cas system) targeting a locus of an endogenous gene other than FIX, respectively, for example, targeting the endogenous albumin gene of a mammal, or primate or human, such as hemophilia patient. In certain embodiments, the therapeutic composition comprises the FIX donor transgene and the albumin gene nuclease in separate, independent vectors, such as separate AAV vectors, in different amounts, which can be administered together (e.g., mixed into a single solution or administered simultaneously) or, alternatively, which can be administered separately ((for example, administered in separate solutions with a substantial delay, e.g., 10 minutes or more, 30 minutes or more, 1 hour or more, 2 hours or more, 3 hours or more, or longer between respective administrations). In certain embodiments, the therapeutic composition is administered to provide integration of the FIX donor transgene into the non-FIX locus and subsequent expression of the integrated FIX to achieve a therapeutic level of FIX in the plasma of the mammal, or primate or human, or hemophilia patient. In certain embodiments, a therapeutic level of FIX can include, for example, greater than 2%, greater than 4%, greater than 5%, greater than 6%, greater than 8%, greater than 10%, greater than 12%, greater than 15%, greater than 20%, greater than 25%, or more of a clinically-acceptable normal plasma concentration of FIX. Alternatively or in addition, a therapeutic level of FIX can include, for example, greater than 2%, greater than 4%, greater than 5%, greater than 6%, greater than 8%, greater than 10%, greater than 12%, greater than 15%, greater than 20%, greater than 25%, greater than 30%, greater than 35%, or more of the plasma concentration of functional FIX measured in the individual mammal, or primate or human, or hemophilia patient prior to administration of the FIX donor transgene and the albumin gene nuclease to that individual.

For targeting the compositions to a particular type of cell, e.g., platelets, fibroblasts, hepatocytes, etc., one or more of the administered compositions may be associated with a homing agent that binds specifically to a surface receptor of the cell. For example, the vector may be conjugated to a ligand (e.g., galactose) for which certain hepatic system cells have receptors. The conjugation may be covalent, e.g., a crosslinking agent such as glutaraldehyde, or noncovalent, e.g., the binding of an avidinated ligand to a biotinylated vector. Another form of covalent conjugation is provided by engineering the AAV helper plasmid used to prepare the vector stock so that one or more of the encoded coat proteins is a hybrid of a native AAV coat protein and a peptide or protein ligand, such that the ligand is exposed on the surface of the viral particle.

A kit, comprising the compositions (e.g., expression vectors, genetically modified cells, ZFPs, CRISPR/Cas system and/or TALENs and optionally transgene donors) of the invention, is also provided. The kit may comprise nucleic acids encoding the nucleases (e.g. RNA molecules or nuclease-encoding genes contained in a suitable expression vector), donor molecules, suitable host cell lines, instructions for performing the methods of the invention, and the like.

These and other aspects will be readily apparent to the skilled artisan in light of disclosure as a whole.

BRIEF DESCRIPTION OF THE DRAWINGS

FIG. 1 is a schematic showing exemplary nucleases and donors. Shown are three vectors: AAV2/6 Vectors for the two nucleases (SB-42906, left ZFN/ZFN 1 and SB-43043, right ZFN/ZFN2) as well as the SB-F9 donor (bottom panel).

FIG. 5A is a schematic representation of alternative mRNA transcripts at the albumin locus. Transcription at the wild type albumin locus (hALB exons 1-8) yields a transcript of 2.3 kb, while after SB-FIX donor integration the fusion transcript hALB (exon1)-hFIX (exons 2-8) is expressed (1.7 kb). The primer binding sites for RT-PCR are depicted. FIG. 5B shows analysis of HepG2 subclones transduced either with SB-FIX donor only or with hALB ZFNs and SB-FIX donor. The top panel shows hFIX secretion from subclones determined by hFIX specific ELISA after 48 hrs secretion. The middle panel shows the mode (HDR or NHEJ) of SB-hFIX donor integration at the human Albumin in all subclones. The bottom panel shows RT-PCR from HepG2 subclones using primers, which are either specific for the wild-type human Albumin transcript or the hALB-hFIX fusion transcript.

FIGS. 6A through 6C show sequences of the hALB ZFNs and an exemplary Factor IX donor as described herein. FIG. 6A shows the amino acid sequence of the ZFN 42906 (SEQ ID NO:15) (ZFP and cleavage domain sequence shown). FIG. 6B shows the amino acid sequence of ZFN 43043 (SEQ ID NO:16) (ZFP and cleavage domain sequence shown). The recognition helix regions of the ZFP are underlined and the FokI cleavage domains are shown in italics ("ELD" FokI domain in ZFN 42906 and "KKR" FokI domain in ZFN 43043). FIG. 6C (SEQ ID NO:17) shows the nucleotide sequence of an exemplary Factor IX donor. The left (base pairs 271-550) and right (base pairs 2121-2220) homology arms are shown in uppercase and underlined. The splice acceptor sequence (base pairs 557-584) is underlined. The codon optimized Factor IX-encoding sequence is shown in uppercase (base pairs 585-1882) and the polyadenylation signal is shown in bold (base pairs 1890-2114).

DETAILED DESCRIPTION

Figure 2:
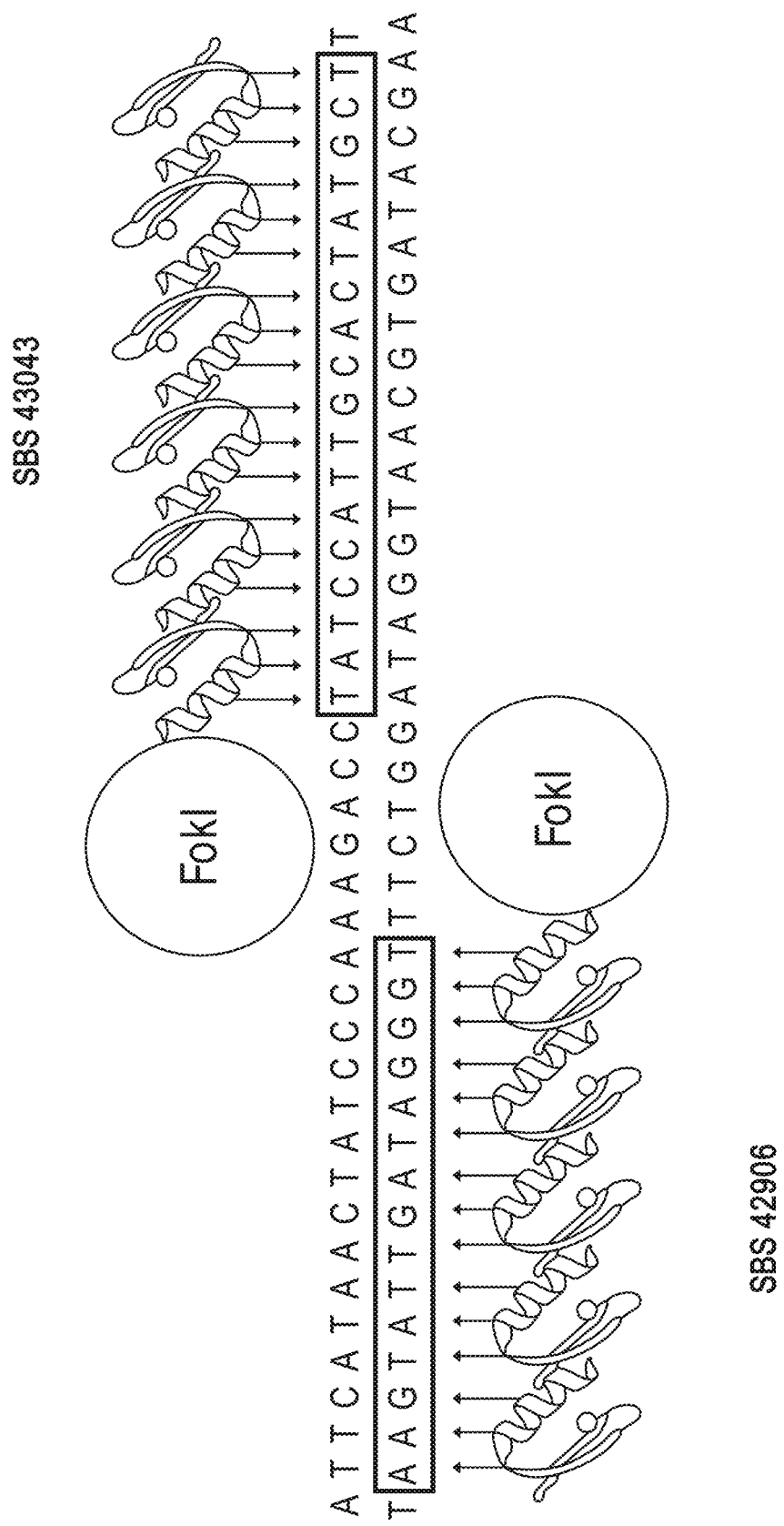
FIG. 2 is a schematic representation showing binding of the ZFNs SBS42906 and SBS43043 to their DNA target sequences (boxed within the albumin sequences shown in SEQ ID NO:1) at the albumin locus.

Disclosed herein are compositions and methods for modifying a cell to produce one or more proteins whose expression or gene sequence, prior to modification, is aberrant. In some embodiments, the protein is associated with a hemophilia. The cell may be modified by targeted insertion of a transgene encoding one or more functional proteins into a safe harbor gene (e.g., albumin) of the cell. In some embodiments, the transgene is inserted into an endogenous albumin gene. The transgene can encode any protein or peptide involved in hemophilia, for example, Factor VII, Factor VIII, Factor IX, Factor X, Factor XI, and/or functional fragments thereof. Also disclosed are methods of treating a hemophilia using a cell as described herein and/or by modifying a cell (ex vivo or in vivo) as described herein. Further described are compositions comprising nucleic acids encoding nucleases and donor molecules for modifying a cell, and methods for modifying the cell in vivo or ex vivo. Additionally, compositions comprising cells that have been modified by the methods and compositions of the invention are described.

The genomically-modified cells described herein are typically modified via nuclease-mediated (ZFN, TALEN and/or CRISPR/Cas) targeted integration to insert a sequence encoding a therapeutic protein (e.g., Factor VII, Factor VIII (F8), Factor IX, Factor X and/or Factor XI), wherein the protein, whose gene in an altered or aberrant state, is associated with a hemophilia disease, into the genome of one or more cells of the subject (in vivo or ex vivo), such that the cells produce the protein in vivo. In certain embodiments, the methods further comprise inducing cells of the subject, particularly liver cells, to proliferate (enter the cell cycle), for example, by partial hepatectomy and/or by administration of one or more compounds that induce hepatic cells to undergo cell cycling. Subjects include but are not limited to humans, non-human primates, veterinary animals such as cats, dogs, rabbits, rats, mice, guinea pigs, cows, pigs, horses, goats and the like.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

The term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, 99%, 99.5%, or 99.8% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, 99%, 99.5%, or 99.8% similar.

The term "identity" refers to the overall relatedness between polymeric molecules, e.g., between nucleic acid molecules (e.g., DNA molecules and/or RNA molecules) and/or between polypeptide molecules. Calculation of the percent identity of two nucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, 99%, 99.5%, 99.8% or substantially 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17), which has been incorporated into the ALIGN program (version 2.0) using a PAM 120 weight residue table, a gap length penalty of 12 and a gap penalty of 4. The percent identity between two nucleotide sequences can, alternatively, be determined using the GAP program in the GCG software package using an NWSgapdna.CMP matrix. Various other sequence alignment programs are available and can be used to determine sequence identity such as, for example, Clustal.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. See, e.g., U.S. Pat. No. 8,586,526.

Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 6,140,081; 6,453,242; 6,534,261; and 8,586,526 see also International Patent Publication Nos. WO 98/53058; WO 98/53059; WO 98/53060; WO 02/016536; and WO 03/016496.

A "selected" zinc finger protein or TALE is a protein not found in nature whose production results primarily from an empirical process such as phage display, interaction trap or hybrid selection. See e.g., U.S. Pat. Nos. 5,789,538; 5,925, 523; 6,007,988; 6,013,453; and 6,200,759; International Patent Publication Nos. WO 95/19431; WO 96/06166; WO 98/53057; WO 98/54311; WO 00/27878; WO 01/60970; WO 01/88197; and WO 02/099084.

"TtAgo" is a prokaryotic Argonaute protein thought to be involved in gene silencing. TtAgo is derived from the bacteria *Thermus thermophilus*. See, e.g., Swarts et al., ibid, G. Sheng et al. (2013) *Proc. Natl. Acad. Sci. U.S.A.* 111: 652). A "TtAgo system" is all the components required including, for example, guide DNAs for cleavage by a TtAgo enzyme.

"Recombination" refers to a process of exchange of genetic information between two polynucleotides, including but not limited to, donor capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein can create a double-stranded break in the target sequence (e.g., cellular chromatin) at a predetermined site, and a "donor" polynucleotide, having homology to the nucleotide sequence in the region of the break, can be introduced into the cell. The presence of the double-stranded break has been shown to facilitate integration of the donor sequence. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. The use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional pairs of zinc-finger proteins or TALEN can be used for additional double-stranded cleavage of additional target sites within the cell.

In certain embodiments of methods for targeted recombination and/or replacement and/or alteration of a sequence in a region of interest in cellular chromatin, a chromosomal sequence is altered by homologous recombination with an exogenous "donor" nucleotide sequence. Such homologous recombination is stimulated by the presence of a double-stranded break in cellular chromatin, if sequences homologous to the region of the break are present.

In any of the methods described herein, the first nucleotide sequence (the "donor sequence") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

Any of the methods described herein can be used for partial or complete inactivation of one or more target sequences in a cell by targeted integration of donor sequence that disrupts expression of the gene(s) of interest. Cell lines with partially or completely inactivated genes are also provided.

Furthermore, the methods of targeted integration as described herein can also be used to integrate one or more exogenous sequences. The exogenous nucleic acid sequence can comprise, for example, one or more genes or cDNA molecules, or any type of coding or noncoding sequence, as well as one or more control elements (e.g., promoters). In addition, the exogenous nucleic acid sequence may produce one or more RNA molecules (e.g., small hairpin RNAs (shRNAs), inhibitory RNAs (RNAis), microRNAs (miR-NAs), etc.).

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Pat. Nos. 7,914,796; 8,034,598; and 8,623,618, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome" is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

A "target site" or "target sequence" is a nucleic acid sequence that defines a portion of a nucleic acid to which a binding molecule will bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP or TALE DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene" for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to an activation domain, the ZFP DNA-binding domain and the activation domain are in operative linkage if, in the fusion polypeptide, the ZFP DNA-binding domain portion is able to bind its target site and/or its binding site, while the activation domain is able to upregulate gene expression. When a fusion polypeptide in which a ZFP DNA-binding domain is fused to a cleavage domain, the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and International Patent Publication No. WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

A "safe harbor" locus is a locus within the genome wherein a gene may be inserted without any deleterious effects on the host cell. Most beneficial is a safe harbor locus in which expression of the inserted gene sequence is not perturbed by any read-through expression from neighboring genes. Non-limiting examples of safe harbor loci that are targeted by nuclease(s) include CCR5, CCR5, HPRT, AAVS1, Rosa and albumin. See, e.g., U.S. Pat. Nos. 7,951,925 and 8,110,379; U.S. Patent Publication Nos. 2008/0159996; 2010/0218264; 2012/0017290; 2011/0265198; 2013/0137104; 2013/0122591; 2013/0177983; and 2013/0177960 and U.S. Provisional Application No. 61/823,689.

Nucleases

Described herein are compositions comprising nucleases, such as nucleases that are useful in integration of a sequence encoding a functional clotting factor (e.g., Factor VIII and/or Factor IX) protein in the genome of a cell from or in a subject with hemophilia A or B. In certain embodiments, the nuclease is naturally occurring. In other embodiments, the nuclease is non-naturally occurring, i.e., engineered in the DNA-binding domain and/or cleavage domain. For example, the DNA-binding domain of a naturally-occurring nuclease may be altered to bind to a selected target site (e.g., a meganuclease that has been engineered to bind to site different than the cognate binding site). In other embodiments, the nuclease comprises heterologous DNA-binding and cleavage domains (e.g., zinc finger nucleases; TAL-effector domain DNA binding proteins; meganuclease DNA-binding domains with heterologous cleavage domains) and/or a CRISPR/Cas system utilizing an engineered single guide RNA).

A. DNA-Binding Domains

Any DNA-binding domain can be used in the compositions and methods disclosed herein, including but not limited to a zinc finger DNA-binding domain, a TALE DNA binding domain, the DNA-binding portion of a CRISPR/Cas nuclease, or a DNA-binding domain from a meganuclease.

In certain embodiments, the nuclease is a naturally occurring or engineered (non-naturally occurring) meganuclease (homing endonuclease). Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. Nos. 5,420,032; 6,833,252; Belfort et al. (1997) *Nucleic Acids Res.* 25:3379-3388; Dujon et al. (1989) *Gene* 82:115-118; Perler et al. (1994) *Nucleic Acids Res.* 22:1125-1127; Jasin (1996) *Trends Genet.* 12:224-228; Gimble et al. (1996) *J Mol. Biol.* 263:163-180; Argast et al. (1998) *J Mol. Biol.* 280:345-353 and the New England Biolabs catalogue. Engineered meganucleases are described for example in U.S. Patent Publication No. 2007/0117128. The DNA-binding domains of the homing endonucleases and meganucleases may be altered in the context of the nuclease as a whole (i.e., such that the nuclease includes the cognate cleavage domain) or may be fused to a heterologous cleavage domain. DNA-binding domains from meganucleases may also exhibit nuclease activity (e.g., cTALENs).

In other embodiments, the DNA-binding domain comprises a naturally occurring or engineered (non-naturally occurring) TAL effector DNA binding domain. See, e.g., U.S. Pat. No. 8,586,526, incorporated by reference in its entirety herein. The plant pathogenic bacteria of the genus *Xanthomonas* are known to cause many diseases in important crop plants. Pathogenicity of *Xanthomonas* depends on a conserved type III secretion (T3S) system which injects more than 25 different effector proteins into the plant cell. Among these injected proteins are transcription activator-like (TAL) effectors which mimic plant transcriptional activators and manipulate the plant transcriptome (see Kay et al. (2007) *Science* 318:648-651). These proteins contain a DNA binding domain and a transcriptional activation domain. One of the most well characterized TAL-effectors is AvrBs3 from *Xanthomonas campestgris* pv. *Vesicatoria* (see Bonas et al. (1989) *Mol Gen Genet* 218:127-136 and International Patent Publication No. WO 2010079430). TAL-effectors contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack et al. (2006) *J Plant Physiol* 163(3):256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer et al. (2007) *Appl and Envir Micro* 73(13):4379-4384). These genes are 98.9% identical in nucleotide sequence to each other but differ by a deletion of 1,575 base pairs in the repeat domain of hpx17. However, both gene products have less than 40% sequence identity with AvrBs3 family proteins of *Xanthomonas*. See, e.g., U.S. Pat. No. 8,586,526, incorporated by reference in its entirety herein.

Specificity of these TAL effectors depends on the sequences found in the tandem repeats. The repeated sequence comprises approximately 102 base pair and the repeats are typically 91-100% homologous with each other (Bonas et al., ibid). Polymorphism of the repeats is usually located at positions 12 and 13 and there appears to be a one-to-one correspondence between the identity of the hypervariable diresidues (the repeat variable diresidue or RVD region) at positions 12 and 13 with the identity of the contiguous nucleotides in the TAL-effector's target sequence (see Moscou and Bogdanove (2009) *Science* 326:1501 and Boch et al. (2009) *Science* 326:1509-1512). Experimentally, the natural code for DNA recognition of these TAL-effectors has been determined such that an HD sequence at positions 12 and 13 (Repeat Variable Diresidue or RVD) leads to a binding to cytosine (C), NG binds to T, NI to A, C, G or T, NN binds to A or G, and ING binds to T. These DNA binding repeats have been assembled into proteins with new combinations and numbers of repeats, to make artificial transcription factors that are able to interact with new sequences and activate the expression of a non-endogenous reporter gene in plant cells (Boch et al., ibid). Engineered TAL proteins have been linked to a FokI cleavage half domain to yield a TAL effector domain nuclease fusion (TALEN), including TALENs with atypical RVDs. See, e.g., U.S. Pat. No. 8,586,526.

In some embodiments, the TALEN comprises a endonuclease (e.g., FokI) cleavage domain or cleavage half-domain. In other embodiments, the TALE-nuclease is a mega TAL. These mega TAL nucleases are fusion proteins comprising a TALE DNA binding domain and a meganuclease cleavage domain. The meganuclease cleavage domain is active as a monomer and does not require dimerization for activity. (See Boissel et al. (2013) *Nucl Acid Res* 42(4):2591-601, doi: 10.1093/nar/gkt1224).

In still further embodiments, the nuclease comprises a compact TALEN. These are single chain fusion proteins linking a TALE DNA binding domain to a TevI nuclease domain. The fusion protein can act as either a nickase localized by the TALE region, or can create a double strand break, depending upon where the TALE DNA binding domain is located with respect to the TevI nuclease domain (see Beurdeley et al. (2013) *Nat Comm* 4:1762:1-8 DOI: 10.1038/ncomms2782). In addition, the nuclease domain may also exhibit DNA-binding functionality. Any TALENs may be used in combination with additional TALENs (e.g., one or more TALENs (cTALENs or FokI-TALENs) with one or more mega-TALEs.

In certain embodiments, the DNA binding domain comprises a zinc finger protein. Preferably, the zinc finger protein is non-naturally occurring in that it is engineered to bind to a target site of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; and 7,253,273; and U.S. Patent Publication Nos. 2005/0064474; 2007/0218528; and 2005/0267061, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as International Patent Publication Nos. WO 98/37186; WO 98/53057; WO 00/27878; and WO 01/88197 and GB 2,338,237. In addition, enhancement of binding specificity for zinc finger binding domains has been described, for example, in co-owned International Patent Publication No. WO 02/077227.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

Selection of target sites; ZFPs and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; and 6,200,759; International Patent Publication Nos. WO 95/19431; WO 96/06166; WO 98/53057; WO 98/54311; WO 00/27878; WO 01/60970; WO 01/88197; WO 02/099084; WO 98/53058; WO 98/53059; WO 98/53060; WO 02/016536; and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

B. Cleavage Domains

Any suitable cleavage domain can be operatively linked to a DNA-binding domain to form a nuclease. such as a zinc finger nuclease, a TALEN, or a CRISPR/Cas nuclease system. See, e.g., U.S. Pat. Nos. 7,951,925; 8,110,379 and 8,586,526; U.S. Patent Publication Nos. 2008/0159996; 2010/00218264; 2012/0017290; 2011/0265198; 2013/0137104; 2013/0122591; 2013/0177983; and 2013/0177960 and U.S. Provisional Patent Application No. 61/823,689.

As noted above, the cleavage domain may be heterologous to the DNA-binding domain, for example a zinc finger DNA-binding domain and a cleavage domain from a nuclease or a TALEN DNA-binding domain and a cleavage domain, or meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., 51 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme FokI catalyzes double-stranded cleavage of DNA, at 9 nucleotides from its recognition site on one strand and 13 nucleotides from its recognition site on the other. See, for example, U.S. Pat. Nos. 5,356,802; 5,436,150; and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is FokI.

This particular enzyme is active as a dimer. Bitinaite et al. (1998) *Proc. Natl. Acad. Sci. USA* 95:10,570-10,575. Accordingly, for the purposes of the present disclosure, the portion of the FokI enzyme used in the disclosed fusion proteins is considered a cleavage half-domain. Thus, for targeted double-stranded cleavage and/or targeted replacement of cellular sequences using zinc finger-FokI fusions, two fusion proteins, each comprising a FokI cleavage half-domain, can be used to reconstitute a catalytically active cleavage domain. Alternatively, a single polypeptide molecule containing a zinc finger binding domain and two FokI cleavage half-domains can also be used. Parameters for targeted cleavage and targeted sequence alteration using zinc finger-FokI fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Patent Publication No. WO 07/014275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 2005/0064474; 2006/0188987; 2007/0305346; and 2008/0131962, the disclosures of all of which are incorporated by reference in their entireties herein. Amino acid residues at positions 446, 447, 479, 483, 484, 486, 487, 490, 491, 496, 498, 499, 500, 531, 534, 537, and 538 of FokI are all targets for influencing dimerization of the FokI cleavage half-domains.

Exemplary engineered cleavage half-domains of FokI that form obligate heterodimers include a pair in which a first cleavage half-domain includes mutations at amino acid residues at positions 490 and 538 of FokI and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E: I499L". The engineered cleavage half-domains described herein are obligate heterodimer mutants in which aberrant cleavage is minimized or abolished. See, e.g., U.S. Pat. Nos. 7,914,796 and 8,034,598, the disclosures of which are incorporated by reference in their entireties for all purposes. In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See U.S. Pat. No. 8,623, 618). In other embodiments, the engineered cleavage half domain comprises the "Sharkey" and/or "Sharkey mutations" (see Guo et al. (2010) *J. Mol. Biol.* 400(1):96-107).

Engineered cleavage half-domains described herein can be prepared using any suitable method, for example, by site-directed mutagenesis of wild-type cleavage half-domains (FokI) as described in U.S. Pat. Nos. 7,888,121; 7,914,796; 8,034,598; and 8,623,618.

Alternatively, nucleases may be assembled in vivo at the nucleic acid target site using so-called "split-enzyme" technology (see, e.g. U.S. Patent Publication No. 2009/0068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in International Patent Publication No. WO 2009/042163 and U.S. Patent Publication No. 2009/0068164. Nuclease expression constructs can be readily designed using methods known in the art. See, e.g., U.S. Patent Publication Nos. 2003/0232410; 2005/0208489; 2005/0026157; 2005/0064474; 2006/0188987; 2006/0063231; and International Patent Publication No. WO 07/014275. Expression of the nuclease may be under the control of a constitutive promoter or an inducible promoter, for example the galactokinase promoter which is activated (de-repressed) in the presence of raffinose and/or galactose and repressed in presence of glucose.

In certain embodiments, the nuclease comprises a CRISPR/Cas system. The CRISPR (clustered regularly interspaced short palindromic repeats) locus, which encodes RNA components of the system, and the cas (CRISPR-associated) locus, which encodes proteins (Jansen et al. (2002) *Mol. Microbiol.* 43:1565-1575; Makarova et al. (2002) *Nucleic Acids Res.* 30:482-496; Makarova et al. (2006) *Biol. Direct* 1:7; Haft et al. (2005) *PLoS Comput. Biol.* 1:e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

Exemplary CRISPR/Cas nuclease systems targeted to safe harbor and other genes are disclosed for example, in U.S. Provisional Patent Application No. 61/823,689.

Thus, the nuclease comprises a DNA-binding domain in that specifically binds to a target site in any gene into which it is desired to insert a donor (transgene).

Target Sites

As described in detail above, DNA-binding domains can be engineered to bind to any sequence of choice, for example in a safe-harbor locus such as albumin. An engineered DNA-binding domain can have a novel binding specificity, compared to a naturally-occurring DNA-binding domain. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties. Rational design of TAL-effector domains can also be performed. See, e.g., U.S. Pat. No. 8,586,526.

Exemplary selection methods applicable to DNA-binding domains, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as International Patent Publication Nos. WO 98/37186; WO 98/53057; WO 00/27878; and WO 01/88197 and GB 2,338,237. In addition, enhancement of binding specificity for zinc finger binding domains has been described, for example, in co-owned International Patent Publication No. WO 02/077227.

Selection of target sites; nucleases and methods for design and construction of fusion proteins (and polynucleotides encoding same) are known to those of skill in the art and described in detail in U.S. Patent Publication Nos. 2005/0064474 and 2006/0188987, incorporated by reference in their entireties herein.

In addition, as disclosed in these and other references, DNA-binding domains (e.g., multi-fingered zinc finger proteins) may be linked together using any suitable linker sequences, including for example, linkers of 5 or more amino acids. See, e.g., U.S. Pat. Nos. 6,479,626; 6,903,185; and 7,153,949 for exemplary linker sequences 6 or more amino acids in length. The proteins described herein may include any combination of suitable linkers between the individual DNA-binding domains of the protein. See, also, U.S. Pat. No. 8,586,526.

For treatment of hemophilia via targeted insertion of a sequence encoding a functional Factor VIII and/or Factor IX protein, any desired site of insertion in the genome of the subject is cleaved with a nuclease, which stimulates targeted insertion of the donor polynucleotide carrying the Factor VIII- and/or Factor IX-encoding sequence. DNA-binding domains of the nucleases may be targeted to any desired site in the genome. In certain embodiments, the DNA-binding domain of the nuclease is targeted to an endogenous safe harbor locus, for example an endogenous albumin locus.

In certain embodiments, a pair of dimerizing zinc finger nucleases as shown in FIGS. 6A and 6B are used for cleavage of an albumin gene to facilitate targeted integration of a Factor IX donor. The ZFNs comprise a DNA-binding domain having the recognition helix regions shown in Table 1 and an engineered FokI cleavage domain such that the ZFNs form an obligate heterodimer (e.g., one member of the pair includes an "ELD" FokI domain and the other member of the pair includes a "KKR" FokI domain).

ZFNs having homology or identity to the ZFNs described herein are also provided, including but not limited to ZFN sequences having at least 25%, 30%, 40%, 50%, 55%, 60%, 65%, 70%, 75%, 80%, 85%, 90%, 95%, 98% sequence homology or identity. Furthermore, it will be understood that the homology is typically determined for residues outside the recognition helix regions, including but not limited to the FokI domain, the linker domain, the zinc finger backbone residues (e.g., any residues outside the recognition helix region). As any zinc finger backbone (context) and/or cleavage domain can be used, significant variation in homology outside the recognition helix regions zinc finger residues can be present.

Donor Sequences

For treating hemophilia, the donor sequence (also called an "exogenous sequence" or "donor" or "transgene") comprises a sequence encoding a functional clotting factor protein, or part thereof, to result in a sequence encoding and expressing a functional clotting factor protein following donor integration. Non-limiting examples of clotting factor protein transgenes include Factor VIII and/or Factor IX, including functional fragments of these proteins. In certain embodiments, the B-domain of the Factor VIII protein is deleted. See, e.g., Chuah et al. (2003) *Blood* 101(5):1734-1743. In other embodiments, the transgene comprises a sequence encoding a functional Factor IX protein, or part thereof, to result in a sequence encoding and expressing a function Factor IX protein following donor integration.

The donor molecule may be inserted into an endogenous gene such that all, some or none of the endogenous gene is expressed. For example, a transgene comprising functional clotting factor protein (e.g., Factor VIII and/or Factor IX) sequences as described herein may be inserted into an endogenous albumin locus such that some or none of the endogenous albumin is expressed with the transgene.

The donor (transgene) sequence can be introduced into the cell prior to, concurrently with, or subsequent to, expression of the fusion protein(s) (e.g., nucleases). The donor polynucleotide may contain sufficient homology (continuous or discontinuous regions) to a genomic sequence to support homologous recombination (or homology-directed repair) between it and the genomic sequence to which it bears homology or, alternatively, donor sequences can be integrated via non-HDR mechanisms (e.g., NHEJ donor capture), in which case the donor polynucleotide (e.g., vector) need not containing sequences that are homologous to the region of interest in cellular chromatin. See, e.g., U.S. Pat. Nos. 7,888,121 and 7,972,843 and U.S. Patent Publication Nos. 2011/0281361; 2010/0047805; and 2011/0207221.

The donor polynucleotide can be DNA or RNA, single-stranded, double-stranded or partially single- and partially double-stranded and can be introduced into a cell in linear or circular (e.g., minicircle) form. See, e.g., U.S. Patent Publication Nos. 2010/0047805; 2011/0281361; and 2011/0207221. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues. A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus).

In some embodiments, the donor may be inserted so that its expression is driven by the endogenous promoter at the integration site (e.g., the endogenous albumin promoter when the donor is integrated into the patient's albumin locus). In such cases, the transgene may lack control elements (e.g., promoter and/or enhancer) that drive its expression (e.g., also referred to as a "promoterless construct"). Nonetheless, it will be apparent that in other cases the donor may comprise a promoter and/or enhancer, for example a constitutive promoter or an inducible or tissue specific (e.g., liver- or platelet-specific) promoter that drives expression of the functional protein upon integration. The donor sequence can be integrated specifically into any target site of choice.

When albumin sequences (endogenous or part of the transgene) are expressed with the transgene, the albumin sequences may be full-length sequences (wild-type or mutant) or partial sequences. Preferably the albumin sequences are functional. Non-limiting examples of the function of these full length or partial albumin sequences include increasing the serum half-life of the polypeptide expressed by the transgene (e.g., therapeutic gene) and/or acting as a carrier.

Furthermore, although not required for expression, exogenous sequences may also include transcriptional or translational regulatory sequences, for example, promoters, enhancers, insulators, internal ribosome entry sites, sequences encoding 2A peptides and/or polyadenylation signals.

Any of the donor sequences may include one or more of the following modifications: codon optimization (e.g., to human codons) and/or addition of one or more glycosylation sites. See, e.g., McIntosh et al. (2013) *Blood* (17):3335-44.

Delivery

The nucleases, polynucleotides encoding these nucleases, donor polynucleotides and compositions comprising the proteins and/or polynucleotides described herein may be delivered in vivo or ex vivo by any suitable means.

Methods of delivering nucleases as described herein are described, for example, in U.S. Pat. Nos. 8,586,526; 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties. Nucleases and/or donor constructs as described herein may also be delivered using vectors containing sequences encoding one or more of the zinc finger protein(s), TALEN protein(s) and/or a CRISPR/Cas system. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more of the sequences needed. Thus, when one or more nucleases and a donor construct are introduced into the cell, the nucleases and/or donor polynucleotide may be carried on the same vector or on different vectors. When multiple vectors are used, each vector may comprise a sequence encoding one or multiple nucleases and/or donor constructs. In certain embodiments, one vector is used to carry both the transgene and nuclease(s). In other embodiments, two vector are used (the same or different vector types), where one vector carries the nuclease(s) (e.g., left and right ZFNs of a ZFN pair, for example with a 2A peptide) and one carries the transgene. In still further embodiments, three vectors are used where the first vector carries one nuclease of a nuclease pair (e.g., left ZFN), the second vector carries the other nuclease of a nuclease pair (e.g., right ZFN) and the third vector carries the transgene. See, FIG. 2.

The donors and/or nuclease may be used at any suitable concentrations. In certain embodiments, the donor and separate nuclease vector(s) are used the same concentration. In other embodiments, the donor and separate nuclease vector(s) are used at different concentrations, for example, 2-, 3-, 4-, 5-, 10-, 15-, 20- or more fold of one vector than other (e.g., more donor vector(s) than nuclease vector(s). For example, a nuclease vector (or nuclease vectors) and a donor vector may be used in a ratio of about 1:1, about 1:2, about 1:3, about 1:4, about 1:5, about 1:6, about 1:7, about 1:8, about 1:9, about 1:10, about 1:11, about 1:12, about 1:13, about 1:14, about 1:15, about 1:16, about 1:17, about 1:18, about 1:19, or, in some cases, about 1:20. In some embodiments, a first nuclease vector, a second nuclease vector that is different from the first nuclease vector, and a donor vector may be used in a ratio of about 1:1:1, about 1:1:2, about 1:1:3, about 1:1:4, about 1:1:5, about 1:1:6, about 1:1:7, about 1:1:8, about 1:1:9, about 1:1:10, about 1:1:11, about 1:1:12, about 1:1:13, about 1:1:14, about 1:1:15, about 1:1:16, about 1:1:17, about 1:1:18, about 1:1:19, or, in some cases, about 1:1:20. In an illustrative embodiment, a first nuclease vector, a second nuclease vector that is different from the first nuclease vector, and a donor vector are used in a ratio of about 1:1:8. When AAV vectors are used for delivery, for example, the donor- and/or nuclease-comprising viral vector(s) may be between about $1 \times 10^8$ and about $1 \times 10^{15}$ vector genomes per kg per dose (e.g., cell or animal).

Conventional viral and non-viral based gene transfer methods can be used to introduce nucleic acids encoding nucleases and donor constructs in cells (e.g., mammalian cells) and target tissues. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of in vivo delivery of engineered DNA-binding proteins and fusion proteins comprising these binding proteins, see, e.g., Rebar (2004) *Expert Opinion Invest. Drugs* 13(7):829-839; Rossi et al. (2007) *Nature Biotech.* 25(12):1444-1454 as well as general gene delivery references such as Anderson (1992) *Science* 256:808-813; Nabel & Felgner (1993) *TIBTECH* 11:211-217; Mitani & Caskey (1993) *TIBTECH* 11:162-166); Dillon (1993) *TIBTECH* 11:167-175; Miller (1992) *Nature* 357:455-460; Van Brunt (1988) *Biotechnology* 6(10):1149-1154; Vigne (1995) *Restorative Neurology and Neuroscience* 8:35-36; Kremer & Perricaudet (1995) *British Medical Bulletin* 51(1):31-44; Haddada et al., in *Current Topics in Microbiology and Immunology* Doerfler and Bohm (eds.) (1995); and Yu et al. (1994) *Gene Therapy* 1:13-26.

Methods of non-viral delivery of nucleic acids include electroporation, lipofection, microinjection, biolistics, virosomes, liposomes, immunoliposomes, polycation or lipid:nucleic acid conjugates, naked DNA, artificial virions, and agent-enhanced uptake of DNA. Sonoporation using, e.g., the Sonitron 2000 system (Rich-Mar) can also be used for delivery of nucleic acids.

Additional exemplary nucleic acid delivery systems include those provided by AmaxaBiosystems (Cologne, Germany), Maxcyte, Inc. (Rockville, Md.), BTX Molecular Delivery Systems (Holliston, Mass.) and Copernicus Therapeutics Inc., (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, International Patent Publication Nos. WO 91/17424, WO 91/16024.

The preparation of lipid:nucleic acid complexes, including targeted liposomes such as immunolipid complexes, is well known to one of skill in the art (see, e.g., Crystal (1995) *Science* 270:404-410; Blaese et al. (1995) *Cancer Gene Ther.* 2:291-297; Behr et al. (1994) *Bioconjugate Chem.* 5:382-389; Remy et al. (1994) *Bioconjugate Chem.* 5:647-654; Gao et al. (1995) *Gene Therapy* 2:710-722; Ahmad et al. (1992) *Cancer Res.* 52:4817-4820; U.S. Pat. Nos. 4,186,183; 4,217,344; 4,235,871; 4,261,975; 4,485,054; 4,501,728; 4,774,085; 4,837,028; and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al. (2009) *Nature Biotechnology* 27(7):643).

The use of RNA or DNA viral based systems for the delivery of nucleic acids encoding engineered nucleases and/or donors take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of nucleases and/or donors include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al. (1992) *J. Virol.* 66:2731-2739; Johann et al. (1992) *J Virol.* 66:1635-1640; Sommerfelt et al. (1990) *Virol.* 176:58-59; Wilson et al. (1989) *J. Virol.* 63:2374-2378; Miller et al. (1991) *J Virol.* 65:2220-2224; International Patent Publication No. WO 94/26877 (PCT/US94/05700)).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al. (1987) *Virology* 160:38-47; U.S. Pat. No. 4,797,368; International Patent Publication No. WO 93/24641; Kotin (1994) *Human Gene Therapy* 5:793-801;

Muzyczka (1994) *J. Clin. Invest.* 94:1351. Construction of recombinant AAV vectors is described in a number of publications, including U.S. Pat. No. 5,173,414; Tratschin et al. (1985)*Mol. Cell. Biol.* 5:3251-3260; Tratschin et al. (1984)*Mol. Cell. Biol.* 4:2072-2081; Hermonat & Muzyczka (1984) *PNAS* 81:6466-6470; and Samulski et al. (1989) *J. Virol.* 63:3822-3828.

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al. (1995) *Blood* 85:3048-305; Kohn et al. (1995) *Nat. Med.* 1:1017-102; Malech et al. (1997) *PNAS* 94:22 12133-12138). PA317/pLASN was the first therapeutic vector used in a gene therapy trial. (Blaese et al. (1995) *Science* 270:475-480). Transduction efficiencies of 50% or greater have been observed for MFG-S packaged vectors. (Ellem et al. (1997) *Immunol Immunother.* 44(1):10-20; Dranoff et al. (1997) *Hum. Gene Ther.* 1:111-2.

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 base pair inverted terminal repeats flanking the transgene expression cassette. Efficient gene transfer and stable transgene delivery due to integration into the genomes of the transduced cell are key features for this vector system. (Wagner et al. (1998) *Lancet* 351(9117): 1702-3; Kearns et al. (1996) *Gene Ther.* 9:748-55). Other AAV serotypes, including AAV1, AAV3, AAV4, AAV5, AAV6, AAV8, AAV9 and AAVrh10 or pseudotyped AAV such as AAV2/8, AAV8.2, AAV2/5 and AAV2/6 and any novel AAV serotype can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al. (1998) *Hum. Gene Ther.* 7:1083-9). Additional examples of the use of adenovirus vectors for gene transfer in clinical trials include Rosenecker et al. (1996) *Infection* 24(1):5-10; Sterman et al. (1998) *Hum. Gene Ther.* 9(7):1083-1089; Welsh et al. (1995) *Hum. Gene Ther.* 2:205-18; Alvarez et al. (1997) *Hum. Gene Ther.* 5:597-613; Topf et al. (1998) *Gene Ther.* 5:507-513; Sterman et al. (1998) *Hum. Gene Ther.* 7:1083-1089.

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al. (1995) *Proc. Natl. Acad. Sci. USA* 92:9747-9751, reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Vectors (e.g., retroviruses, adenoviruses, liposomes, etc.) containing nucleases and/or donor constructs can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Vectors suitable for introduction of polynucleotides (e.g. nuclease-encoding and/or Factor VII, Factor VIII, FIX, Factor X and/or Factor XI-encoding) described herein include non-integrating lentivirus vectors (IDLV). See, for example, Ory et al. (1996) *Proc. Natl. Acad. Sci. USA* 93:11382-11388; Dull et al. (1998) *J. Virol.* 72:8463-8471;

Zuffery et al. (1998) *J. Virol.* 72:9873-9880; Follenzi et al. (2000) *Nature Genetics* 25:217-222; U.S. Patent Publication No. 2009/054985.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences,* 17th ed., 1989).

It will be apparent that the nuclease-encoding sequences and donor constructs can be delivered using the same or different systems. For example, the nucleases and donors can be carried by the same vector (e.g., AAV). Alternatively, a donor polynucleotide can be carried by a plasmid, while the one or more nucleases can be carried by a different vector (e.g., AAV vector). Furthermore, the different vectors can be administered by the same or different routes (intramuscular injection, tail vein injection, other intravenous injection, intraperitoneal administration and/or intramuscular injection. The vectors can be delivered simultaneously or in any sequential order.

Thus, in certain embodiments, the instant disclosure includes in vivo or ex vivo treatment of Hemophilia A, via nuclease-mediated integration of Factor VIII-encoding sequence. The disclosure also includes in vivo or ex vivo treatment of Hemophilia B, via nuclease-mediated integration of a Factor IX encoding sequence. Similarly, the disclosure includes the treatment of Factor VII deficiency, Factor X, or Factor XI deficiency related hemophilias via nuclease-mediated integration of a Factor VII, Factor X, or Factor XI encoding sequence, respectively. The compositions are administered to a human patient in an amount effective to obtain the desired concentration of the therapeutic Factor VII, Factor VIII, Factor IX or Factor X polypeptide in the serum, the liver or the target cells. Administration can be by any means in which the polynucleotides are delivered to the desired target cells. For example, both in vivo and ex vivo methods are contemplated. Intravenous injection to the portal vein is a preferred method of administration. Other in vivo administration modes include, for example, direct injection into the lobes of the liver or the biliary duct and intravenous injection distal to the liver, including through the hepatic artery, direct injection in to the liver parenchyma, injection via the hepatic artery, and/or retrograde injection through the biliary tree. Ex vivo modes of administration include transduction in vitro of resected hepatocytes or other cells of the liver, followed by infusion of the transduced, resected hepatocytes back into the portal vasculature, liver parenchyma or biliary tree of the human patient, see e.g., Grossman et al. (1994) *Nature Genetics* 6:335-341. Other modes of administration include the ex vivo nuclease-mediated insertion of a Factor VII, Factor VIII, Factor IX, Factor X and/or Factor XI encoding transgene into a safe harbor location into patient or allogenic stem cells. Following modification, the treated cells are then re-infused into the patient for treatment of a hemophilia.

Treatment of hemophilias is discussed herein by way of example only, and it should be understood that other conditions may be treating using the methods and compositions disclosed herein. In some cases, the methods and composition may be useful in the treatment of thrombotic disorders. The effective amount of nuclease(s) and Factor VII, Factor VIII, Factor IX, Factor X, or Factor XI donor to be administered will vary from patient to patient and according to the therapeutic polypeptide of interest. Accordingly, effective amounts are best determined by the physician administering the compositions and appropriate dosages can be determined readily by one of ordinary skill in the art. After allowing sufficient time for integration and expression (typically 4-15 days, for example), analysis of the serum or other tissue levels of the therapeutic polypeptide and comparison to the initial level prior to administration will determine whether the amount being administered is too low, within the right range or too high. In some embodiments, a single dose may be administered to a patient. In some embodiments, multiple doses may be administered to a patient. In some embodiments, co-administration of the compositions disclosed herein with other therapeutic agents may be performed.

Suitable regimes for initial and subsequent administrations are also variable, but are typified by an initial administration followed by subsequent administrations if necessary. Subsequent administrations may be administered at variable intervals, ranging from daily to annually to every several years. One of skill in the art will appreciate that appropriate immunosuppressive techniques may be recommended to avoid inhibition or blockage of transduction by immunosuppression of the delivery vectors, see e.g., Vilquin et al. (1995) *Human Gene Ther.* 6:1391-1401.

Formulations for both ex vivo and in vivo administrations include suspensions in liquid or emulsified liquids. The active ingredients often are mixed with excipients which are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

The following Examples relate to exemplary embodiments of the present disclosure in which the nuclease comprises a zinc finger nuclease (ZFN). It will be appreciated that this is for purposes of exemplification only and that other nucleases can be used, for instance homing endonucleases (meganucleases) with engineered DNA-binding domains and/or fusions of naturally occurring of engineered homing endonucleases (meganucleases) DNA-binding domains and heterologous cleavage domains, TALENs and/or a CRISPR/Cas system comprising an engineered single guide RNA.

EXAMPLES

Example 1: Nuclease and Donor Construction

To target the human albumin locus two individual ZFNs, SBS42906 (5-finger protein) and SBS43043 (6-finger protein) were designed to bind adjacent 15 base pair and 18 base pair target sites, respectively, with high affinity and specificity. The ZFNs are shown below in Table 1.

Uppercase in the target sequence denotes bound nucleotides and lowercase denotes unbound nucleotides.

TABLE 1

Albumin specific ZFNs

Design

Albumin specific ZFNs

| SBS #, Target | F1 | F2 | F3 | F4 | F5 | F6 |
|---|---|---|---|---|---|---|
| SBS# 42906 ttTGGGATAGTTA TGAAttcaatctt ca (SEQ ID NO: 2) | QSGNLAR (SEQ ID NO: 4) | LKQNLCM (SEQ ID NO: 5) | WADNLQN (SEQ ID NO: 6) | TSGNLTR (SEQ ID NO: 7) | RQSHLCL (SEQ ID NO: 8) | NA |
| SBS#43043 ccTATCCATTGCA CTATGCTttattt aa (SEQ ID NO: 3) | TPQLLDR (SEQ ID NO: 9) | LKWNLRT (SEQ ID NO: 10) | DQSNLRA (SEQ ID NO: 11) | RNFSLTM (SEQ ID NO: 12) | LRHDLDR (SEQ ID NO: 13) | HRSNLNK (SEQ ID NO: 14) |

The strict requirement of both ZFNs being bound to a combined 33 base pair recognition sequence in a specific spatial orientation on the DNA provides the functional specificity necessary to catalyze the formation of a double-strand break (DSB) at a single pre-determined site in the albumin locus. A schematic representation of this architecture is shown in FIG. 2. The two ZFNs are each targeted to a specific sequence in an intronic region of the albumin gene (nucleotides 447-485 relative to the transcription start site) located on opposite strands of DNA.

A FokI nuclease cleavage domain is attached to the carboxy-terminal end of each ZFP. See, e.g., U.S. Pat. Nos. 7,888,121 and 8,623,618. An additional feature of the FokI domain that enforces highly specific function is the restriction of cleavage only to heterodimer binding events. This is achieved through the use of variant FokI domains (e.g., "ELD/KKR") that have been engineered to function only as heterodimers. See, e.g., U.S. Pat. No. 8,623,618. These obligate heterodimer FokI domains prevent off-target cleavage at potential homodimer sites, thus further enhancing ZFN specificity.

Donor vectors were constructed as follows. The rAAV2/6 vectors encoding the ZFNs targeting the albumin intron 1 locus and hF9 transgene are shown in FIG. 1. For the two ZFN encoding AAV2/6 vectors, SB-42906 and SB-43043 (expressing the left and right ZFN respectively), ZFN expression is under control of a liver-specific enhancer and promoter, comprised of the human ApoE enhancer and human α1-anti-trypsin (hAAT) promoter (Miao et al. (2000) *Mol. Ther.* 1(6):522-532). The ApoE/hAAT promoter is highly active in hepatocytes, the intended target tissue, but is inactive in other cell and tissue types to prevent ZFN expression and activity in non-target tissues.

The rAAV2/6 donor vector containing the hF9 transgene (SB-F9 donor) is a promoterless construct that encodes a partial hF9 cDNA comprising exons 2-8. The F9 exon 2 splice acceptor site (SA) is present to allow efficient splicing of hF9 transgene (exons 2-8) into the mature mRNA from the albumin locus, regardless of the mechanism of integration (NHEJ or HDR; see, e.g., FIGS. 3 and 4). Optionally flanking the hF9 transgene are sequences homologous to the cleavage site at the albumin intron 1 locus. The left arm of homology (LA) contains 280 nucleotides of identical sequence upstream of the albumin intron 1 cleavage site, and the right arm of homology (RA) contains 100 nucleotides of identical sequence downstream of the cleavage site. The arms of homology are used to help facilitate targeted integration of the hF9 transgene at the albumin intron 1 locus via homology-directed repair. The sizes of the homology arms were chosen to avoid repetitive sequences and splicing elements in the albumin locus that can inhibit targeted integration or transgene expression. The PolyA sequences are derived from the Bovine Growth Hormone gene. The rAAV vectors are packaged with capsid serotype AAV2/6 using a Baculovirus (Sf9) expression system.

Example 2: Nuclease Modification in Human Primary Hepatocytes

One day after plating, human primary hepatocytes were transduced with either one or two ZFN expressing rAAV2/6 virus(es) at an MOI of 0.3E5-9.0E5 vector genomes (vg) per cell. Cells were harvested at Day 7 and genomic DNA and protein were prepared for both percent indels (insertions and/or deletions) analysis by miSEQ and ZFN expression analysis by Western blot using an antibody against the FokI domain.

The ZFNs described herein (SBS42906 (5-finger; left ZFN) and SBS43043 (6-finger; right ZFN)) exhibited high levels of modification (e.g., between 10-30% indels).

Figure 3:
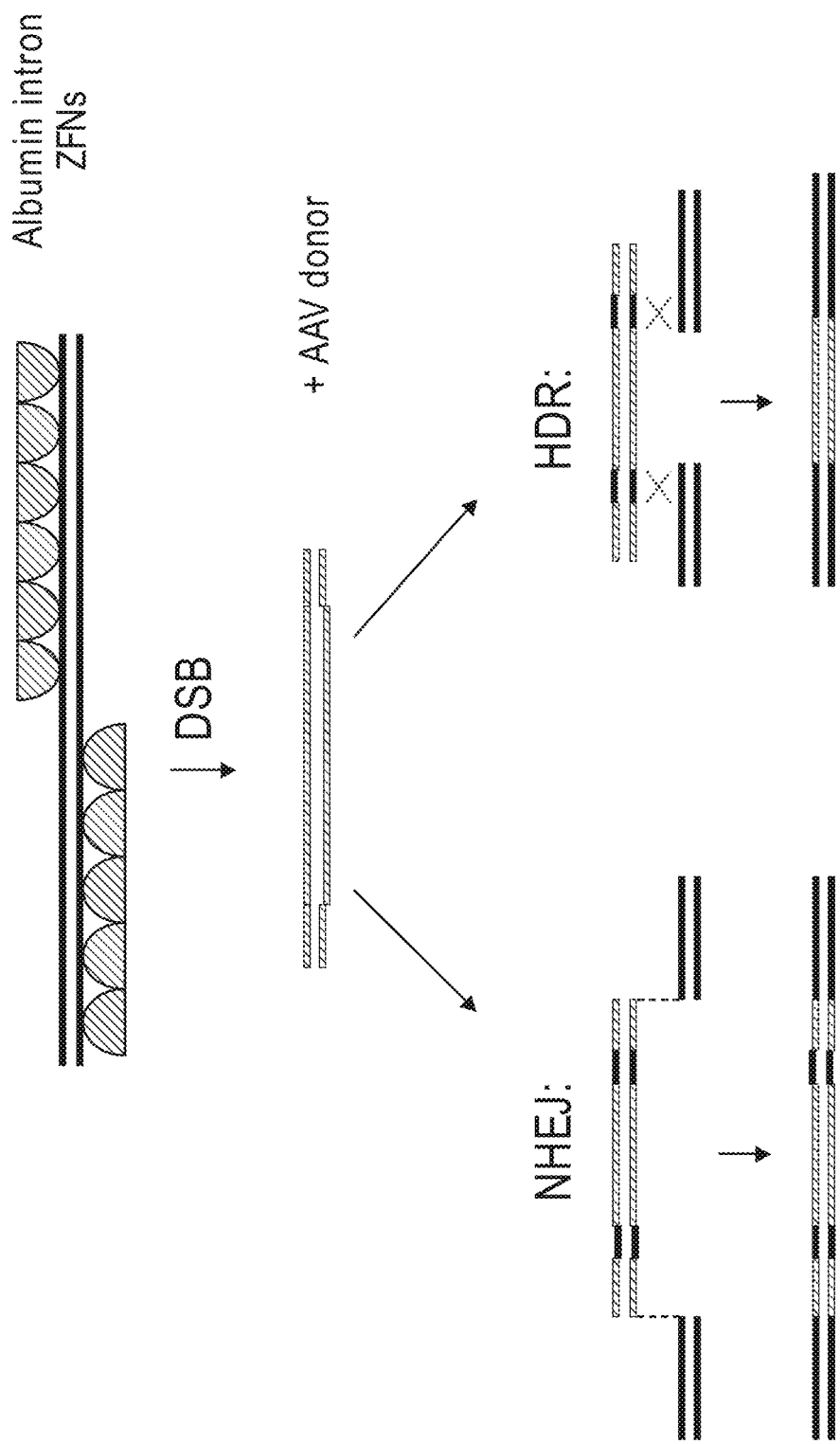
FIG. 3 is a schematic depicting nuclease-mediated homology and non-homology directed targeted integration.
Figure 4:
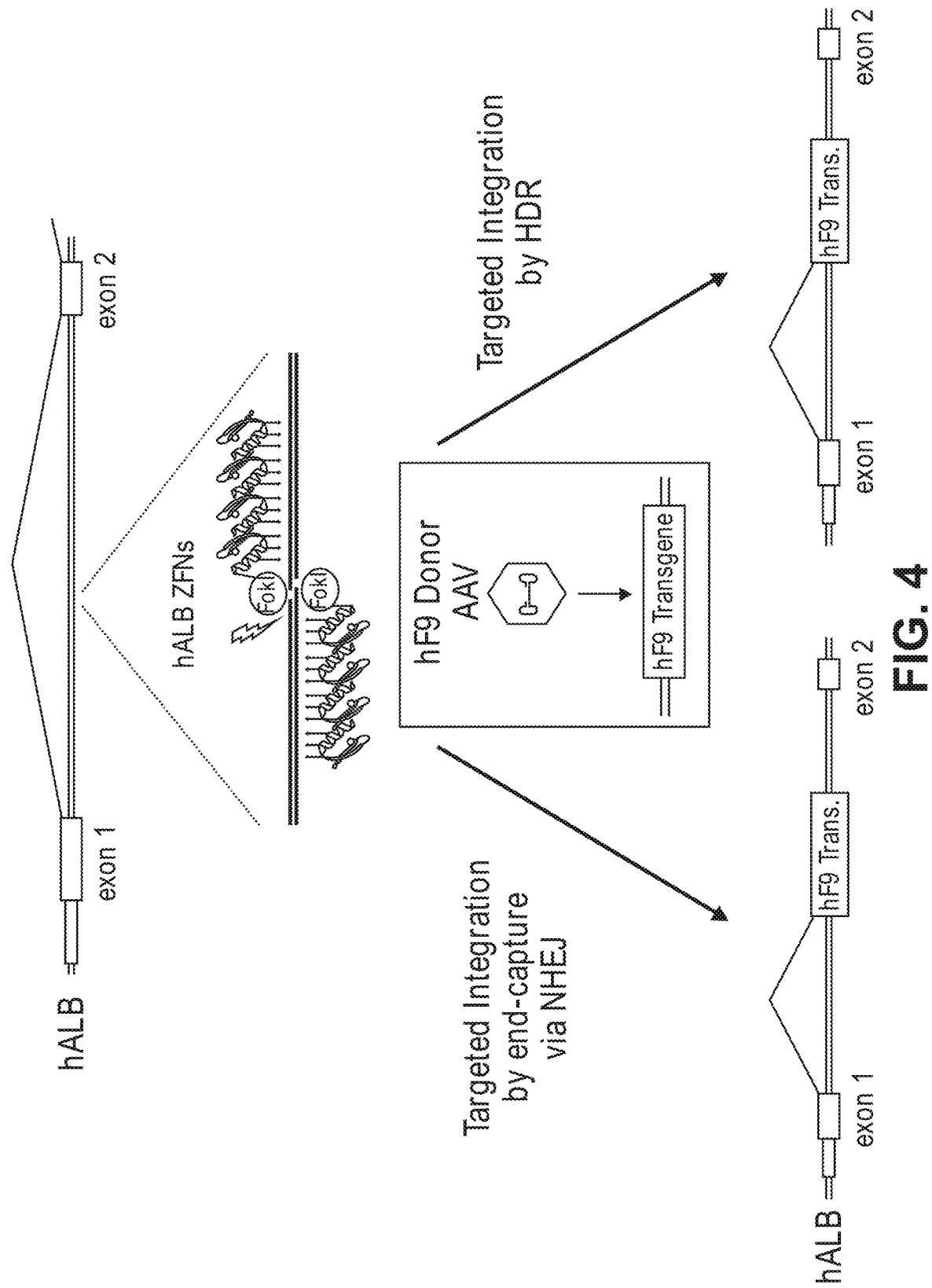
FIG. 4 is a schematic depicting targeted integration of the hF9 donor by either NHEJ or HDR. Regardless of the mechanism by which targeted integration occurs (NHEJ on the left and HDR on the right), the splice acceptor sequence encoded by the donor allows for proper mRNA splicing and expression of the hF9 transgene (exons 2-8) to exon 1 from the Endogenous Albumin Promoter.

In addition, a human hepatoma cell line (HepG2) was used to evaluate specific nuclease-mediated integration at the albumin locus and mode of integration (NHEJ or HDR). HepG2 cells transduced with human albumin ZFNs and FIX donor showed strong hFIX secretion (~75 ng/ml) above background, and analysis of albumin-specific gene modification by miSEQ showed ~74% indels. Subclones were used for genotyping to determine the specific integration at the albumin locus and the mode of integration either by NHEJ or HDR (FIG. 3). Subclones also showed strong hFIX secretion (up to 350 ng/ml). Overall, there was no difference between subclones with monoallelic donor integration by either HDR or NHEJ.

These results showed that hFIX can be stably expressed from the albumin locus independent of the mode of FIX donor integration.

Figure 5A:
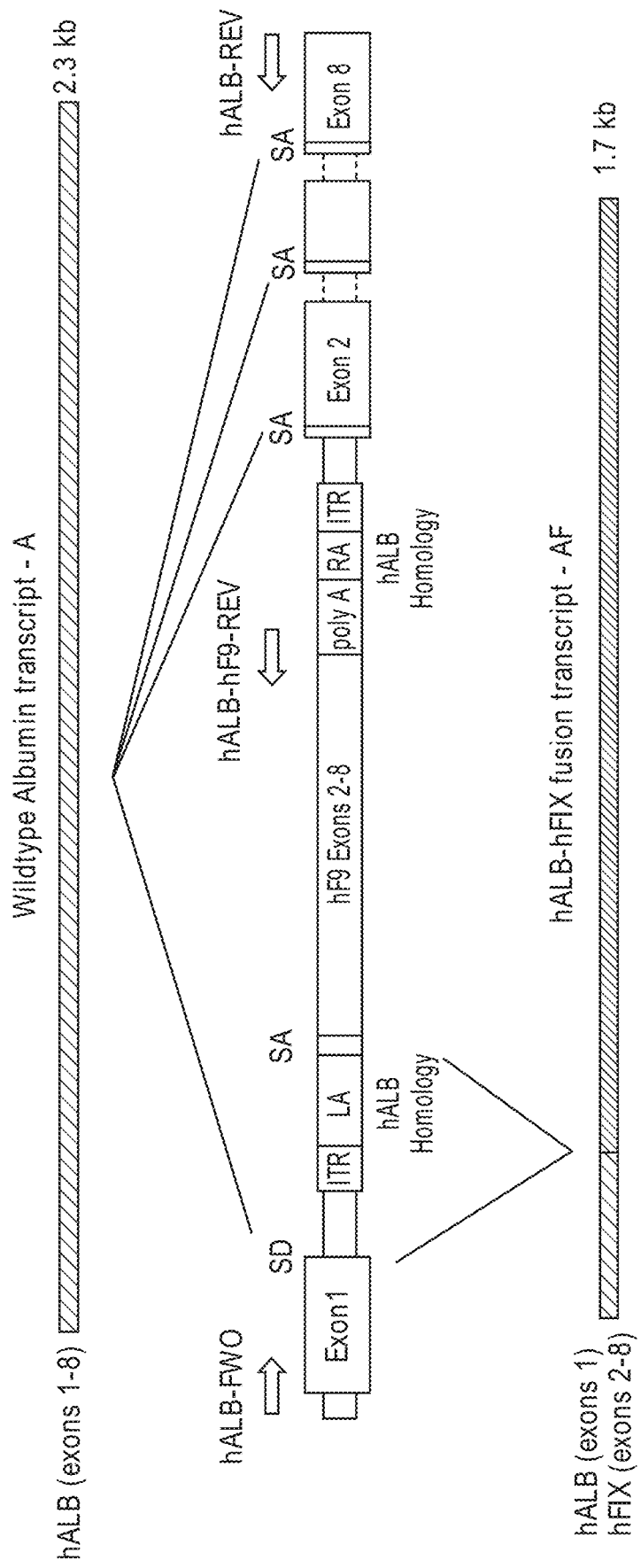
FIGS. 5A and 5B show of mRNA transcripts at the Albumin locus.

After stable integration of the FIX donor at the albumin locus, the hALB-hFIX fusion protein mRNA is transcribed from the albumin promoter. While expression of the unaltered wild type Albumin gene leads to a 2.3 kb transcript, the hALB-hFIX fusion mRNA is shorter with 1.7 kb (FIG. 5A) independently of the integration mode by either NHEJ or HDR.

Figure 5B:
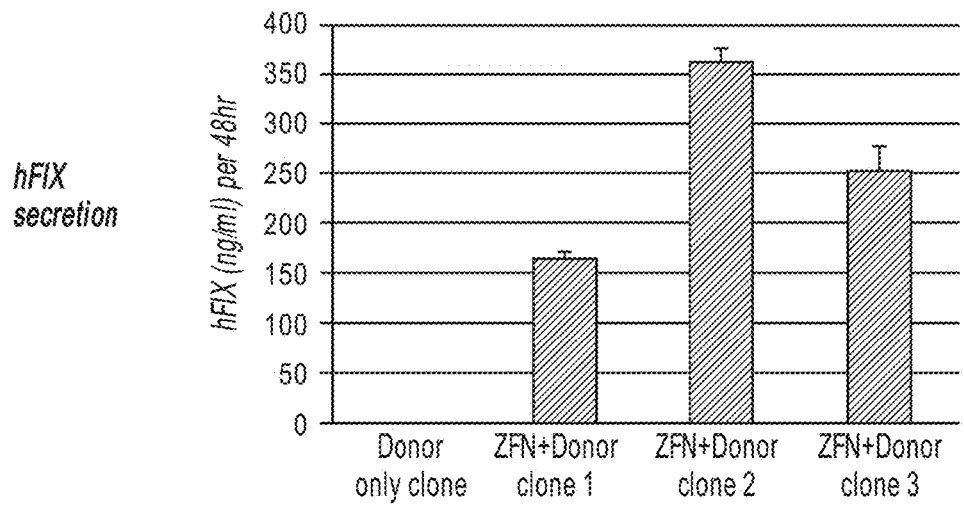
Figure 5B:
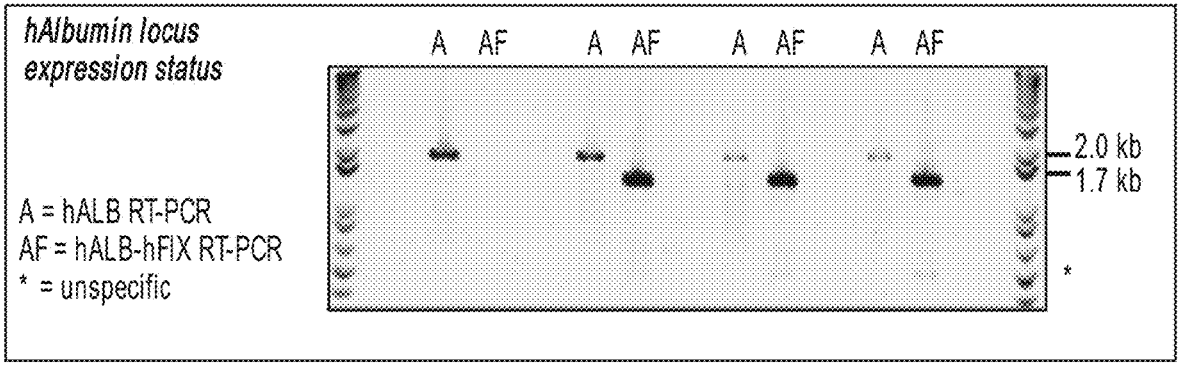

We demonstrated this by creating stable subclones of the Hepatoma cell line HepG2 with stably integrated FIX donors either by NHEJ or HDR. After transduction of HepG2 cells with SB-42906, SB-43043 and FIX donor we identified by integration-specific genotyping several subclones, which exhibited FIX donor integration by either NHEJ or HDR and which showed high (150-350 ng/ml) secreted levels of hFIX proteins detectable by hFIX ELISA (FIG. 5B). After total mRNA isolation and reverse transcription to cDNA we analyzed the transcripts of these subclones by PCR and sequencing. In unmodified control cells we could only detect the expected wild type Albumin transcript (2.3 kb) with primers flanking the exon 1-8, but no transcript with primers binding to the FIX donor.

In three HepG2 subclones that have the FIX donor integrated into the albumin locus and secrete FIX, we detected both the wild type human albumin transcript and with primers binding to the Albumin 5'UTR and the FIX donor 3'UTR the expected hALB-hFIX fusion transcript (1.7 kb). Subcloning and sequencing of these RT-PCR products confirmed that it is the expected hAlb-hFIX fusion mRNA. This suggests that in all three subclones the FIX donor integrated either by NHEJ or HDR in one Albumin allele which led to the expression of a functional hALB-hFIX transcript and further secreted hFIX protein. MiSeq analysis of the other allele showed that these subclones carried a 10 or 40 nucleotide (nt) deletion or a 1 nt insertion in albumin intron1. Despite these indels, the cells as expected produce about half the amount of wild-type albumin transcript and protein as the unmodified control cells, demonstrating that small indels in albumin exon1 have no major impact on albumin expression. Since in these subclones there were no other transcripts detectable with primers binding to exon8 of the albumin mRNA, we concluded that after hFIX donor integration mRNA splicing occurs only between the splice donor site of the Albumin exon1 and the splice acceptor site of the hF9 donor.

In summary, our detailed analysis of the transcription profile at the nuclease-modified albumin locus in HepG2 subclones showed that only the desired hALB-hFIX fusion protein mRNA is expressed.

Successful targeted integration requires all three AAV vectors to transduce the same hepatocyte (see for example, U.S. Provisional Patent Application No. 61/943,865). We have found that the efficiency of targeted integration is dependent on the ratio of ZFN:Donor. Thus, the rAAV-encoded ZFN vectors are formulated at a 1:1 ratio, and the rAAV-encoded ZFN:ZFN:hF9 donor DNA ratio is 1:1:8.

Example 3: In Vitro Off-Target SELEX-Guided Toxicity Evaluation in Humans

A bioinformatics approach was used to identify potential off-target effects of ZFN action by searching the genome for best-fit matches to the intended DNA binding sites for the ZFNs as described herein. To obtain a consensus preference binding site for each ZFN, an affinity-based target site selection procedure known as SELEX (systemic evolution of ligands by experimental enrichment) was employed.

Briefly, the SELEX experiment was performed by incubating the ZFP portion of the ZFN with a pool of random DNA sequences, capturing the ZFP protein and any bound DNA sequences via affinity chromatography, and then PCR amplifying the bound DNA fragments. These DNA fragments were cloned and sequenced and aligned to determine the consensus binding preference.

These experimentally derived preferences for every position in the 15 base pair and 18 base pair binding sites for the two ZFNs of Table 1 were then used to guide a genome-wide bioinformatics search for the most similar sites in the human genome. The resulting list of potential cleavage sites was then ranked to give priority to those sites with the highest similarity to the SELEX-derived consensus sequences. The top 40 sites in the human genome were identified. Of these 40 sites, 18 fell within annotated genes, but only 1 of these occurred within exonic (protein coding) sequences. Low levels of modification at an intronic sequence would not be expected to impact gene expression or function.

Next, to determine if these sites are cleaved by the nucleases described herein, human primary hepatocytes and the human hepatoma cell line HepG2 were transduced with high doses (3e5 vg/cell) of SB-42906 and SB-43043 (both packaged as AAV2/6) or an AAV2/6 vector expressing GFP as control. Genomic DNA was isolated 7-9 days post-transfection, and the on-target (hALB intron 1 locus) and top 40 predicted off-target site loci were PCR amplified from 100 ng of genomic DNA (~15,000 diploid genomes). The level of modification at each locus was then determined by paired-end deep sequencing on an Illumina miSEQ. Paired sequences were merged via the open source software package SeqPrep (developed by Dr. John St. John, for example see Klevegring et al. (2014) *PLOS One* doi: e104417 doi.10, 1371journal.pone 0104417).

Each sequence was filtered for a quality score of ≥15 across all bases, then mapped to the human genome (hg19 assembly). Sequences which mapped to an incorrect locus were removed from further analysis. A Needleman-Wunsch (Needleman, S. B. and Wunsch, C. D. (1970) *J. Mol Biol* 48(3):443-53) alignment was performed between the target amplicon genome region and the obtained Illumina Miseq read to map insertions and deletions. Indel events in aligned sequences were defined as described in Gabriel et al. (2011) *Nature Biotechnology*. 29(9):816-23 except that indels 1 base pair in length were also considered true indels to avoid undercounting real events.

After application of the described analysis the on-target modification was measured at 16.2% indels in human primary hepatocytes and 30.0% indels in HepG2 cells. No significant indels could be detected at any of the potential top 40 off-target sites in either cell type.

These results highlight the exquisite specificity of the ZFN reagents SBS42906 and SBS43043 in both human primary hepatocyte and hepatoma cells at on-target levels (16 and 30%, respectively).

Example 4: In Vivo Targeted Integration

The nucleases (and/or polynucleotides encoding the nucleases) and donors and/or pharmaceutical compositions comprising the nucleases and/or donors as described herein are administered to a human subject such that a corrective FIX transgene is integrated into the subject's genome (e.g., under the control of, the subject's own endogenous albumin locus), thus resulting in liver-specific synthesis of Factor IX. In particular, male subjects, at least 18 years of age, with severe Hemophilia B (>6 hemorrhages/year when untreated) who are receiving prophylactic FIX replacement therapy (>100 doses) as per current treatment guideline without inhibitors to FIX and have no hypersensitivity to recombinant FIX are administered nucleases and FIX donors as described herein according to one of the following schedules illustrated in Table 2:

TABLE 2

| ZFN 1 (vg/kg) | ZFN 2 (vg/kg) | cDNA Donor (vg/kg) | Total rAAV Dose (vg/kg) |
|---|---|---|---|
| 5.00E+11 | 5.00E+11 | 4.00E+12 | 5.00E+12 |
| 1.00E+12 | 1.00E+12 | 8.00E+12 | 1.00E+13 |
| 5.00E+12 | 5.00E+12 | 4.00E+13 | 5.00E+13 |
| 1.00E+13 | 1.00E+13 | 8.00E+13 | 1.00E+14 |

* ZFN1:ZFN2:cDNA Donor Ratio used: 1:1:8 ZFN1:ZFN2:cDNA Donor ratio

"SB-FIX" contains three components, namely three individual recombinant adeno-associated virus (rAAV) serotype 2/6 (rAAV2/6) vectors, administered as an intravenous dose: a first vector (SB-42906) encoding SBS42906 (designated the left ZFN and herein referred to as ZFN1), a second vector (SB-43043) encoding SBS43043 (designated the right ZFN and herein referred to as ZFN2), and a third vector (hF9 gene donor) encoding a DNA repair template encoding a promoterless hF9 transgene.

The 3 components of SB-FIX (2 nucleases and donor) are administered sequentially and/or concurrently, for example in one or more pharmaceutical compositions, via intravenous infusion (e.g., portal vein).

Optionally subjects are treated (before, during and/or after SB-FIX administration) with immunosuppressive agents such as corticosteriods, for example to reduce or eliminate immune responses (e.g., neutralizing antibody (NAB) responses or immune responses to AAV). In particular, subjects who develop increased liver aminotransferases will be administered a brief immunosuppressive regimen with 60 mg of prednisolone followed by a taper over 4-6 weeks.

Subjects are evaluated for an immune response to AAV2/6; an immune response to FIX; the presence of AAV2/6 vector DNA; the presence of albumin locus gene modifications (modification site of SB-FIX) by PCR in blood, saliva, urine, stool and semen; change from baseline in FIX levels; change from baseline in aPTT; any change from baseline in use of Factor IX replacement therapy; any change from baseline in frequency and/or severity of bleeding episodes; and liver function (including, for example, AST, ALT, bilirubin, alkaline phosphatase, and albumin levels).

SB-FIX administration restores hepatic production of functional FIX. At >1% of normal levels, the need for prophylactic treatment with FIX concentrate is reduced or eliminated and at >5% of normal, hemorrhage following all but the most severe trauma is substantially reduced. AAV-mediated gene transfer of the FIX cDNA into liver cells thus provides long term production of FIX in Hemophilia B subjects.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A cell comprising a sequence encoding a Factor IX (F.IX) protein integrated into intron 1 of an endogenous albumin gene such that the F.IX protein is expressed from the albumin gene.

2. The cell of claim 1, wherein the cell is a liver cell.

3. A method of treating a patient with hemophilia B, the method comprising generating a cell according to claim 2 in the patient, thereby treating the patient.

4. The method of claim 3, wherein the cell is generated in the patient by administering at least one polynucleotide comprising sequences encoding a nuclease and the F.IX protein.

5. The method of claim 4, wherein the nuclease comprises a zinc finger nuclease (ZFN), a TAL-effector domain nuclease (TALEN) or a CRISPR/Cas nuclease system.

6. The method of claim 5, wherein the nuclease comprises a ZFN comprising first and second zinc finger nucleases, the first zinc finger nuclease comprising a FokI cleavage domain and a zinc finger protein comprising 5 zinc finger domains ordered F1 to F5, wherein each zinc finger domain comprises a recognition helix region and wherein the recognition helix regions of the zinc finger protein are SEQ ID NOs: 4, 5, 6, 7, and 8, and the second zinc finger nuclease comprising a FokI cleavage domain and a zinc finger protein comprising 6 zinc finger domains ordered F1 to F6, wherein each zinc finger domain comprises a recognition helix region and wherein the recognition helix regions of the zinc finger protein are SEQ ID NOs: 9, 10, 11, 12, 13, and 14.

7. The method of claim 4, wherein the at least one polynucleotide encoding the nuclease and the F.IX protein is administered intravenously to the patient.

8. The method of claim 4, wherein first, second and third polynucleotides are administered to the patient, the first polynucleotide encoding a first zinc finger nuclease, the second polynucleotide encoding a second zinc finger protein and the third polynucleotide comprising the sequence encoding the F.IX protein and further wherein the first and second zinc finger nuclease dimerize to form a zinc finger nuclease.

9. The method of claim 8, wherein the first, second and third polynucleotides are carried on AAV vectors.

10. The method of claim 8, wherein the first, second and third polynucleotides are administered in a ratio of about 1:1:1, about 1:1:2, about 1:1:3, about 1:1:4, about 1:1:5, about 1:1:6, about 1:1:7, about 1:1:8, about 1:1:9, about 1:1:10, about 1:1:11, about 1:1:12, about 1:1:13, about 1:1:14, about 1:1:15, about 1:1:16, about 1:1:17, about 1:1:18, about 1:1:19, or about 1:1:20.

11. The method of claim 9, wherein the AAV vectors are administered in a ratio about 1:1:1, about 1:1:2, about 1:1:3, about 1:1:4, about 1:1:5, about 1:1:6, about 1:1:7, about 1:1:8, about 1:1:9, about 1:1:10, about 1:1:11, about 1:1:12, about 1:1:13, about 1:1:14, about 1:1:15, about 1:1:16, about 1:1:17, about 1:1:18, about 1:1:19, or about 1:1:20.

* * * * *

SEQUENCE LISTING

```
<160> NUMBER OF SEQ ID NOS: 17

<210> SEQ ID NO 1
<211> LENGTH: 41
<212> TYPE: DNA
<213> ORGANISM: Homo sapiens

<400> SEQUENCE: 1
attcataact atcccaaaga cctatccatt gcactatgct t                    41

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tttgggatag ttatgaattc aatcttca                                   28

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cctatccatt gcactatgct ttatttaa                                   28
```

-continued

```
<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Ser Gly Asn Leu Ala Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Leu Lys Gln Asn Leu Cys Met
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Trp Ala Asp Asn Leu Gln Asn
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Thr Ser Gly Asn Leu Thr Arg
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Gln Ser His Leu Cys Leu
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 9

Thr Pro Gln Leu Leu Asp Arg
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Leu Lys Trp Asn Leu Arg Thr
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Gln Ser Asn Leu Arg Ala
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Asn Phe Ser Leu Thr Met
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Leu Arg His Asp Leu Asp Arg
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

His Arg Ser Asn Leu Asn Lys
1               5
```

-continued

```
<210> SEQ ID NO 15
<211> LENGTH: 342
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Ala Glu Arg Pro Phe Gln Cys Arg Ile Cys Met Arg Asn Phe Ser
1               5                   10                  15

Gln Ser Gly Asn Leu Ala Arg His Ile Arg Thr His Thr Gly Glu Lys
            20                  25                  30

Pro Phe Ala Cys Asp Ile Cys Gly Arg Lys Phe Ala Leu Lys Gln Asn
        35                  40                  45

Leu Cys Met His Thr Lys Ile His Thr Gly Glu Lys Pro Phe Gln Cys
    50                  55                  60

Arg Ile Cys Met Arg Lys Phe Ala Trp Ala Asp Asn Leu Gln Asn His
65                  70                  75                  80

Thr Lys Ile His Thr Gly Glu Lys Pro Phe Gln Cys Arg Ile Cys Met
                85                  90                  95

Arg Asn Phe Ser Thr Ser Gly Asn Leu Thr Arg His Ile Arg Thr His
            100                 105                 110

Thr Gly Glu Lys Pro Phe Ala Cys Asp Ile Cys Gly Arg Lys Phe Ala
        115                 120                 125

Arg Gln Ser His Leu Cys Leu His Thr Lys Ile His Leu Arg Gly Ser
    130                 135                 140

Gln Leu Val Lys Ser Glu Leu Glu Glu Lys Lys Ser Glu Leu Arg His
145                 150                 155                 160

Lys Leu Lys Tyr Val Pro His Glu Tyr Ile Glu Leu Ile Glu Ile Ala
                165                 170                 175

Arg Asn Ser Thr Gln Asp Arg Ile Leu Glu Met Lys Val Met Glu Phe
            180                 185                 190

Phe Met Lys Val Tyr Gly Tyr Arg Gly Lys His Leu Gly Gly Ser Arg
        195                 200                 205

Lys Pro Asp Gly Ala Ile Tyr Thr Val Gly Ser Pro Ile Asp Tyr Gly
    210                 215                 220

Val Ile Val Asp Thr Lys Ala Tyr Ser Gly Gly Tyr Asn Leu Pro Ile
225                 230                 235                 240

Gly Gln Ala Asp Glu Met Glu Arg Tyr Val Glu Glu Asn Gln Thr Arg
                245                 250                 255

Asp Lys His Leu Asn Pro Asn Glu Trp Trp Lys Val Tyr Pro Ser Ser
            260                 265                 270

Val Thr Glu Phe Lys Phe Leu Phe Val Ser Gly His Phe Lys Gly Asn
        275                 280                 285

Tyr Lys Ala Gln Leu Thr Arg Leu Asn His Ile Thr Asn Cys Asn Gly
    290                 295                 300

Ala Val Leu Ser Val Glu Glu Leu Leu Ile Gly Gly Glu Met Ile Lys
305                 310                 315                 320

Ala Gly Thr Leu Thr Leu Glu Glu Val Arg Arg Lys Phe Asn Asn Gly
                325                 330                 335

Glu Ile Asn Phe Arg Ser
            340
```

<210> SEQ ID NO 16
<211> LENGTH: 407
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

Met Glu Thr Ala Pro Lys Lys Arg Lys Val Gly Ile His Gly Val
1               5                   10                  15

Pro Ala Ala Met Glu Thr Ala Glu Arg Pro Phe Gln Cys Arg Ile Cys
            20                  25                  30

Met Glu Thr Arg Asn Phe Ser Thr Pro Gln Leu Leu Asp Arg His Ile
        35                  40                  45

Arg Thr His Thr Gly Glu Lys Pro Phe Ala Cys Asp Ile Cys Gly Arg
    50                  55                  60

Lys Phe Ala Leu Lys Trp Asn Leu Arg Thr His Thr Lys Ile His Thr
65                  70                  75                  80

Gly Glu Lys Pro Phe Gln Cys Arg Ile Cys Met Glu Thr Arg Asn Phe
                85                  90                  95

Ser Asp Gln Ser Asn Leu Arg Ala His Ile Arg Thr His Thr Gly Glu
            100                 105                 110

Lys Pro Phe Ala Cys Asp Ile Cys Gly Arg Lys Phe Ala Arg Asn Phe
        115                 120                 125

Ser Leu Thr Met Glu Thr His Thr Lys Ile His Thr Gly Glu Arg Gly
    130                 135                 140

Phe Gln Cys Arg Ile Cys Met Glu Thr Arg Asn Phe Ser Leu Arg His
145                 150                 155                 160

Asp Leu Asp Arg His Ile Arg Thr His Thr Gly Glu Lys Pro Phe Ala
                165                 170                 175

Cys Asp Ile Cys Gly Arg Lys Phe Ala His Arg Ser Asn Leu Asn Lys
            180                 185                 190

His Thr Lys Ile His Leu Arg Gly Ser Gln Leu Val Lys Ser Glu Leu
        195                 200                 205

Glu Glu Lys Lys Ser Glu Leu Arg His Lys Leu Lys Tyr Val Pro His
    210                 215                 220

Glu Tyr Ile Glu Leu Ile Glu Ile Ala Arg Asn Ser Thr Gln Asp Arg
225                 230                 235                 240

Ile Leu Glu Met Glu Thr Lys Val Met Glu Thr Glu Phe Phe Met Glu
                245                 250                 255

Thr Lys Val Tyr Gly Tyr Arg Gly Lys His Leu Gly Gly Ser Arg Lys
            260                 265                 270

Pro Asp Gly Ala Ile Tyr Thr Val Gly Ser Pro Ile Asp Tyr Gly Val
        275                 280                 285

Ile Val Asp Thr Lys Ala Tyr Ser Gly Gly Tyr Asn Leu Pro Ile Gly
    290                 295                 300

Gln Ala Asp Glu Met Glu Thr Gln Arg Tyr Val Lys Glu Asn Gln Thr
305                 310                 315                 320

Arg Asn Lys His Ile Asn Pro Asn Glu Trp Trp Lys Val Tyr Pro Ser
                325                 330                 335

Ser Val Thr Glu Phe Lys Phe Leu Phe Val Ser Gly His Phe Lys Gly
            340                 345                 350

Asn Tyr Lys Ala Gln Leu Thr Arg Leu Asn Arg Lys Thr Asn Cys Asn
        355                 360                 365

Gly Ala Val Leu Ser Val Glu Glu Leu Leu Ile Gly Gly Glu Met Glu
    370                 375                 380

Thr Ile Lys Ala Gly Thr Leu Thr Leu Glu Glu Val Arg Arg Lys Phe
385                 390                 395                 400

Asn Asn Gly Glu Ile Asn Phe
                405

<210> SEQ ID NO 17
<211> LENGTH: 2496
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

| | | | | | |
|---|---|---|---|---|---|
| ctgcgcgctc | gctcgctcac | tgaggccgcc | cgggcaaagc | ccgggcgtcg | ggcgaccttt | 60 |
| ggtcgcccgg | cctcagtgag | cgagcgagcg | cgcagagagg | gagtggccaa | ctccatcact | 120 |
| aggggttcct | gcggcctaag | cttgagcgga | gttccaattg | tactgtacag | aaccatggtc | 180 |
| acatgtttaa | cgctagcgtg | ccgacctggt | aaactgatca | gtgggtgcac | ttaggactgc | 240 |
| gtcttacgct | aatcacatgc | gtgcggccgc | tttattctat | tttcccagta | aaataaagtt | 300 |
| ttagtaaact | ctgcatcttt | aaagaattat | tttggcattt | atttctaaaa | tggcatagta | 360 |
| ttttgtattt | gtgaagtctt | acaaggttat | cttattaata | aaattcaaac | atcctaggta | 420 |
| aaaaaaaaaa | aaggtcagaa | ttgtttagtg | actgtaattt | tcttttgcgc | actaaggaaa | 480 |
| gtgcaaagta | acttagagtg | actgaaactt | cacagaatag | ggttgaagat | tgaattcata | 540 |
| actatcccaa | ggtaccacta | agaattatt | cttttacatt | tcagttttc | ttgatcatga | 600 |
| aaacgccaac | aaaatcctga | accggcccaa | gcggtacaac | tcaggcaagc | tggaagagtt | 660 |
| cgtgcagggc | aacctggaac | gggagtgcat | ggaagagaag | tgcagcttcg | aggaagcccg | 720 |
| ggaggtgttc | gagaacaccg | agcggaccac | cgagttctgg | aagcagtacg | tggacggcga | 780 |
| ccagtgcgag | tcaaacccct | gcctgaacgg | cggcagctgc | aaggacgata | tcaacagcta | 840 |
| cgagtgctgg | tgccccttcg | gcttcgaggg | caagaactgc | gagctggacg | tgacctgcaa | 900 |
| catcaagaac | ggccgctgcg | agcagttctg | caagaacagc | gccgacaaca | aggtggtgtg | 960 |
| ctcatgcact | gagggctacc | ggctggccga | gaaccagaag | agctgcgagc | ccgccgtgcc | 1020 |
| cttcccctgc | ggcagagtgt | ccgtgagcca | gaccagcaag | ctgaccaggg | ccgaggccgt | 1080 |
| gttccctgac | gtggactacg | tgaactcaac | cgaggccgag | acaatcctgg | acaacatcac | 1140 |
| ccagagcacc | cagtccttca | cgacttcac | ccgggtggtg | ggcggcgagg | acgccaagcc | 1200 |
| cggccagttc | ccttggcagg | tggtgctgaa | cggcaaggtg | gacgccttct | gcggcggctc | 1260 |
| aatcgtgaac | gagaagtgga | tcgtgacagc | cgcccactgc | gtggagacag | gcgtgaagat | 1320 |
| caccgtggtg | gccggcgaac | acaatatcga | ggaaaccgag | cacaccgagc | agaaacggaa | 1380 |
| cgtgatccgg | attatccccc | accacaacta | caacgccgcc | atcaacaagt | acaaccacga | 1440 |
| tatcgccctg | ctggaactgg | acgagcctct | ggtgctgaat | tcatacgtga | cccccatctg | 1500 |
| tatcgccgac | aaagagtaca | ccaacatctt | tctgaagttc | ggcagcggct | acgtgtccgg | 1560 |
| ctggggcagg | gtgttccaca | agggccgcag | cgccctggtg | ctgcagtacc | tgcgggtgcc | 1620 |
| cctggtggac | agagccacct | gcctgcggtc | aaccaagttc | accatctaca | acaacatgtt | 1680 |
| ctgcgccggc | ttccacgagg | gcggcaggga | cagctgccag | ggcgacagcg | gcggacccca | 1740 |
| cgtgaccgag | gtggagggca | ccagcttcct | gaccggcatc | atctcatggg | gcgaggaatg | 1800 |

```
cgccatgaag ggcaagtacg gaatctacac taaggtgtca agatacgtga actggatcaa    1860
agagaaaacc aagctgacct gagtttaaac tgtgccttct agttgccagc catctgttgt    1920
ttgcccctcc cccgtgcctt ccttgaccct ggaaggtgcc actcccactg tcctttccta    1980
ataaaatgag gaaattgcat cgcattgtct gagtaggtgt cattctattc tggggggtgg    2040
ggtggggcag gacagcaagg gggaggattg ggaagacaat agcaggcatg ctggggatgc    2100
ggtgggctct atggaccggt ctatccattg cactatgctt tatttaaaaa ccacaaaacc    2160
tgtgctgttg atctcataaa tagaacttgt atttatattt attttcattt tagtctgtct    2220
ggatccacaa attaatcgaa cctgcagctg atatcgacgc ttaagtaggg cttagcaaac    2280
gcgtctccaa cgtttcgccg ttaacacccc acatagtgag tggtcttagt agtccgggtg    2340
tttaaactga aagataactc gagcgcagga accctagtg atggagttgg ccactccctc    2400
tctgcgcgct cgctcgctca ctgaggccgg gcgaccaaag gtcgcccgac gcccgggctt    2460
tgcccgggcg gcctcagtga gcgagcgagc gcgcag                              2496
```